United States Patent [19]

Ellar et al.

[11] Patent Number: 4,918,006

[45] Date of Patent: Apr. 17, 1990

[54] GENE CODING FOR INSECTICIDAL CRYSTAL PROTEIN

[75] Inventors: David J. Ellar, Kingston; Elizabeth S. Ward, Cambridge, both of England

[73] Assignee: E. I. Du Pont de Nemours and Company, Wilmington, Del.

[21] Appl. No.: 824,912

[22] Filed: Feb. 3, 1986

Related U.S. Application Data

[63] Continuation-in-part of Ser. No. 750,211, Jul. 1, 1985, abandoned.

[51] Int. Cl.$^4$ .............. C12P 21/00; C12N 15/00; C07H 15/12
[52] U.S. Cl. ................. 435/69.1; 435/172.3; 435/252.31; 435/252.33; 435/320; 935/9; 935/23; 935/29; 536/27
[58] Field of Search ........... 435/68, 70, 317, 320, 435/172.3, 250; 424/93, 94; 536/27; 935/9, 23, 29

[56] References Cited

U.S. PATENT DOCUMENTS

4,467,036 8/1984 Schneof et al. .............. 435/317
4,514,502 4/1985 Miwa et al. .................. 435/253

OTHER PUBLICATIONS

Ward et al. Febs. (1984) vol. 175, #2, pp. 377–382.
Davidson et al. (1984) Curr. Microbiol. 11 pp. 171–174.
Sekar et al. May 1, 1985, vol. 33, #2, pp. 151–158.
Weng et al. J. Biol. Chem. (1983) vol. 258, #2, pp. 1960–1967.

*Primary Examiner*—Thomas G. Wiseman
*Assistant Examiner*—Patricia Carson
*Attorney, Agent, or Firm*—James A. Costello

[57] ABSTRACT

Recombinant plasmids containing the larvicidal delta-endotoxin gene were constructed by inserting HindIII fragments of the *Bacillus thuringiensis* var. *israelensis* 72-75 Md plasmid into the *Escherichia coli* vector pUC12. Two recombinants producing a 27-kdal toxin (pIP173 and pIP174) were identified by screening clones in an *E. coli* in vitro transcription-translation system. Both recombinants comprised pUC12 and common 9.7 kb HindIII fragment of the *B. thuringiensis* plasmid. The 27,340 Da polypeptide synthesized in vito from pIP174 transformed into *E. coli* JM101 and from *B. subtilis* 168 and spoOJ87 containing the 1.2 kb TaqI fragment from pIP173 was lethal to mosquito larvae.

12 Claims, 11 Drawing Sheets

FIG. 3

| BASE NUMBER | SITE |
|---|---|
| 1 | TaqI |
| 151 | AccI |
| 220-226 | Promoter |
| 240-246 | Promoter |
| 257 | Ribosome binding site |
| 266 | Transcription start sites |
| 286 | Transcription start sites |
| 296 | Start codon |
| 393 | Bam HI |
| 717 | Pst I |
| 952 | HincII |
| 1043-1045 | Stop codon |

FIG. 4(a)

SEQUENCE NUMBER 1            MOLLUSC

```
TCGAACTATAGCGCATAGAATACTACGGTGAATCAAAAACAAATAAAATTTAGGAGGTAT
     10        20        30        40        50        60

ATTCAAGTATACAAAAAAACTTTAGTGTGAGGGGATTTAGATAAAAAGTATTCGTTATCC
     70        80        90       100       110       120

TTATAAATTAATTCTTAAACATGCACCAATGTATACATTAAATAATATTATGTGAATTAA
    130       140       150       160       170       180

GTCTATCAATTTAATTTATTATGTTACTTTATATTTGATTAATAATTGCAAGTTTAAAAT
    190       200       210       220       230       240

M  E
CATAATTTAATGTTGAAAGGCCACTATTCTAATTAACTTAAGGAGTTGTTTATTTATGGA
    250       260       270       280       290       300

N  L  N  H  C  P  L  E  D  I  K  V  N  P  W  K  T  P  Q  S
AAATTTAAATCATTGTCCATTAGAAGATATAAAGGTAAATCCATGGAAAACCCCTCAATC
    310       320       330       340       350       360

T  A  R  V  I  T  L  R  V  E  D  P  N  E  I  N  N  L  L  S
AACAGCAAGGGTTATTACATTACGTGTTGAGGATCCAAATGAAATCAATAATCTTCTTTC
    370       380       390       400       410       420

I  N  E  I  D  N  P  N  Y  I  L  Q  A  I  M  L  A  N  A  F
TATTAACGAAATTGATAATCCGAATTATATATTGCAAGCAATTATGTTAGCAAATGCATT
    430       440       450       460       470       480

Q  N  A  L  V  P  T  S  T  D  F  G  D  A  L  R  F  S  M  P
TCAAAATGCATTAGTTCCCACTTCTACAGATTTTGGTGATGCCCTACGCTTTAGTATGCC
    490       500       510       520       530       540

K  G  L  E  I  A  N  T  I  T  P  M  G  A  V  V  S  Y  V  D
AAAAGGTTTAGAAATCGCAAACACAATTACACCGATGGGTGCTGTAGTGAGTTATGTTGA
    550       560       570       580       590       600
```

FIG. 4(a) Continued

```
     Q  N  V  T  Q  T  N  N  Q  V  S  V  M  I  N  K  V  L  E  V
TCAAAATGTAACTCAAACGAATAACCAAGTAAGTGTTATGATTAATAAAGTCTTAGAAGT
     610       620       630       640       650       660

L  K  T  V  L  G  V  A  L  S  G  S     V  I  D  Q  L  T  A  A
GTTAAAAACTGTATTAGGAGTTGCATTAAGTGGATCTGTAATAGATCAATTAACTGCAGC
     670       680       690       700       710       720

V  T  N  T  F  T  N  L  N  T  Q  K  N  E  A  W  I  F  W  G
AGTTACAAATACGTTTACAAATTTAAATACTCAAAAAAATGAAGCATGGATTTTCTGGGG
     730       740       750       760       770       780

K  E  T  A  N  Q  T  N  Y  T  Y  N     V  L  F  A  I  Q  N  A
CAAGGAAACTGCTAATCAAACAAATTACACATACAATGTCCTGTTTGCAATCCAAAATGC
     790       800       810       820       830       840

Q  T  G  G  V  M  Y  C  V  P  V  G  F  E  I  K  V  S  A  V
CCAAACTGGTGGCGTTATGTATTGTGTACCAGTTGGTTTTGAAATTAAAGTATCAGCAGT
     850       860       870       880       890       900

K  E  Q  V  L  F  F  T  I  Q  D  S     A  S  Y  N  V  N  I  Q
AAAGGAACAAGTTTTATTTTTCACAATTCAAGATTCTGCGAGCTACAATGTTAACATCCA
     910       920       930       940       950       960

S  L  K  F  A  Q  P  L  V  S  S  S  Q  Y  P  I  A  D  L  T
ATCTTTGAAATTTGCACAACCATTAGTTAGCTCAAGTCAGTATCCAATTGCAGATCTTAC
     970       980       990       1000      1010      1020

S  A  I  N  G  T  L
TAGCGCTATTAATGGAACCCTCTAA
     1030      1040
```

FIG. 4(b)

```
TAQI
|
TTTTCGATTTCAAATTTTCCAAACTTAAATATGATTGAATGCCTGAGAAAGGTAATAGAG
        10        20        30        40        50        60

ATGTTTTAGTTTATTATGAAGTATTAGGGGCGTCTTTTAAATTCAATCTATCAATTTGTG
        70        80        90       100       110       120
                                                    PEC1

AAATATATTACTCAAAACCCAATACCATTCTAAAACTTATTCAAAATATATATTGCTTTA
       130       140       150       160       170       180

TAQI
                               |
AAGAGCATACATACTAAAAAAACAGGCATCTTTCGAACTATAGCCGCATAGAATACTACG
       190       200       210       220       230       240
                                                          PS1

GTGAATCAAAAACAAATAAAATTTAGGAGGTATATTCAAGTATACAAAAAAACTTTAGTG
       250       260       270       280       290       300

TGAGGGGATTTAGATAAAAAGTATTCGTTATCCTTATAAATTAATTCTTAAACATGCACG
       310       320       330       340       350       360

AATGTATACATTAAATAATATTATGTGAATTAAGTCTATCAATTTAATTTATTATGTTAC
       370       380       390       400       410       420
                              PBS2

TTTATATTTGATTAATAATTGCAAGTTTAAAATCATAATTTAATGTTGAAAGGCCACTAT
       430       440       450       460       470       480
                                                          PBS1

M   E   N   L   N   H   C   P   L   E   D
TCTAATTAACTTAAGGAGTTGTTTATTTATGGAAAATTTAAATCATTGTCCATTAGAAGA
       490       500       510       520       530       540

I   K   V   N   P   W   K   T   P   Q   S   T   A   R   V   I   T   L   R   V
TATAAAGGTAAATCCATGGAAAACCCCTCAATCAACAGCAAGGGTTATTACATTACGTGT
       550       560       570       580       590       600

E   D   P   N   E   I   N   N   L   L   S   I   N   E   I   D   N   P   N   Y
TGAGGATCCAAATGAAATCAATAATCTTCTTTCTATTAACGAAATTGATAATCCGAATTA
       610       620       630       640       650       660
```

FIG. 4(b) Continued

```
        I   L   Q   A   I   M   L   A   N   A   F   Q   N   A   L   V   P   T   S   T
       TATATTGCAAGCAATTATGTTAGCAAATGCATTTCAAAATGCATTAGTTCCCACTTCTAC
            670       680       690       700       710       720

D   F   G   D   A   L   R   F   S   M   P   K   G   L   E   I   A   N   T   I
       AGATTTGGTGATGCCCTACGCTTTAGTATGCCAAAAGGTTTAGAAATCGCAAACACAAT
            730       740       750       760       770       780

T   P   M   G   A   V   V   S   Y   V   D   Q   N   V   T   Q   T   N   N   Q
       TACACCGATGGGTGCTGTAGTGAGTTATGTTGATCAAAATCTAACTCAAACGAATAACCA
            790       800       810       820       830       840

V   S   V   M   I   N   K   V   L   E   V   L   K   T   V   L   G   V   A   L
       AGTAAGTGTTATGATTAATAAAGTCTTAGAAGTGTTAAAAACTGTATTAGGAGTTGCATT
            850       860       870       880       890       900

S   G   S   V   I   D   Q   L   T   A   A   V   T   N   F   T   N   L   N
       AAGTGGATCTGTAATACATCAATTAACTGCAGCAGTTACAAATACGTTTACAAATTTAAA
            910       920       930       940       950       960

T   Q   K   N   K   A   W   I   F   W   G   K   K   T   A   N   Q   T   N   Y
       TACTCAAAAAAATGAAGCATGGATTTTCTGGGGCAAGGAAACTGCTAATCAAACAAATTA
            970       980       990      1000      1010      1020

T   Y   N   V   L   F   A   I   Q   N   A   Q   T   G   G   V   M   Y   C   V
       CACATACAATGTCCTGTTTGCAATCCAAAATGCCCAAACTGGTGGCCTTATGTATTGTCT
           1030      1040      1050      1060      1070      1080

P   V   G   F   E   I   K   V   S   A   V   K   E   Q   V   L   F   F   T   I
       ACCAGTTGGTTTTGAAATTAAAGTATCAGCAGTAAAGGAACAAGTTTTATTTTTCACAAT
           1090      1100      1110      1120      1130      1140

Q   D   S   A   S   Y   N   V   N   I   Q   S   L   K   F   A   Q   P   L   V
       TCAAGATTCTGCGAGCTACAATGTTAACATCCAATCTTTGAAATTTGCACAACCATTAGT
           1150      1160      1170      1180      1190      1200

S   S   S   Q   Y   P   I   A   D   L   T   S   A   I   N   G   T   L   •
       TAGCTCAAGTCACTATCCAATTGCAGATCTTACTAGCGCTATTAATGGAACCCTCTAATC
           1210      1220      1230      1240      1250      1260
```

FIG. 4(b) Continued

```
TTAGTAGCTATATTTATTAAATTGGTAATATCACAAGTATAAATACTTGTGGTATTACC
    1270      1280      1290      1300      1310      1320

TACCATTCTTAAATTATATCCAAAATCATGCGTTAATCTACATTCCCCTTTCTCTAAAAT
    1330      1340      1350      1360      1370      1380

TTGTTCTTCACACATCCACATTTTTCGA
    1390      1400       |
                         |
                        TAQ I
```

FIG. 5 (a)

-pIPI73/-pIPI74 RESTRICTION MAP (Not To Scale)

(9.7kb HindIII Fragment of B.thuringiensis var. israelensis inserted into pUC12)

——— pUC12 DNA a———▶b  B.thuringiensis var. israelensis DNA

4,918,006

GENE CODING FOR INSECTICIDAL CRYSTAL PROTEIN

CROSS-REFERENCE TO RELATED APPLICATIONS

This application is a continuation-in-part of U.S. Ser. No. 750,211, filed July 1, 1981 now abandoned.

BACKGROUND OF THE INVENTION

1. Field of the Invention

The present invention relates to a gene containing a DNA composition having the nucleotide base sequence coding for a 27-kdal protein of *Bacillus thuringiensis* with insecticidal properties, microorganisms transformed with such DNA, insecticidal compositions containing the protein or transformed microorganisms and to use of said compositions for control of insects, especially Diptera in the larval form.

2. Description of the Prior Art

The gram-positive bacterium *Bacillus thuringiensis* var. *israelensis* (Goldberg, L. J. and Margalitt, J. (1977) *Mosquito News*, 37 355-358) produces a cytolytic protein delta-endotoxin that is lethal to the larvae of mosquitoes and blackfly (diptera) (De Barjac, H (1978) C.R. Acad. Sci. Paris, ser. D 286, 797-800; Thomas, W. E. and Ellar, D. J. (1983) *J. Cell Sci.*, 60 181-197). This delta-endotoxin is synthesized during sporulation as part of a parasporal crystalline protein inclusion (Somerville, H. J. (1978), *Trends Biochem. Sci.*, 108-110; Bulla, L. A., Jr., Bechtel, D. B., Kramer, K. J., Shethna, Y., Aronson, A. I. and Fitz-James, P. C. (1980) *CRC Crit. Rev. Microb.*, 8, 147-204). A combination of the potent activity of this *israelensis* delta-endotoxin against dipteran disease vectors, with the fact that protein delta-endotoxins produced by other serotypes of *B. thuringiensis* are highly toxic to a wide range of lepidopteran pest insects (Luthy, P. (1980) *FEMS Microb. Lett.*, 8, 1-7), has provoked considerable scientific and commercial interest in these bacteria over the past 30 years.

Recent reports of the isolation and expression of the delta-endotoxin gene of *B. thuringiensis* var. *kurstaki* (Schnepf, H.E. and Whiteley, H. R. (1981) *Proc. Natl. Acad. Sci. USA*, 78, 2893-2897; Held, G. A., Bulla, L. A., Jr., Ferrari, E., Hoch, J., Aronson, A. I. and Minnich, S. A. (1982) *Proc. Natl. Acad. Sci. USA*, 79, 6065-6069) and var. *berliner* (Klier, A., Fargette, F., Ribier, J. and Rapoport, G. (1982) *EMBO J.*, 1, 791-799) indicate that the delta-endotoxin gene may be variously located on plasmid DNA, chromosomal DNA, or both (Schnepf, H. E. and Whiteley, H. R. (1981) *Proc. Natl. Acad. Sci. USA*, 78, 2893-2897; Held, G. A., Bulla, L. A., Jr., Ferrari, E., Hoch, J., Aronson, A. I. and Minnich, S. A. (1982) *Proc. Natl. Acad. Sci. USA*, 79, 6065-6069; Klier, A., Fargette, F., Ribier, J. and Rapoport, G. (1982) *EMBO J.*, . 1, 791-799; Kronstad, J. W., Schnepf, H. E. and Whiteley, H. R. (1983) *J. Bacteriol.*, 154, 419-428; Gonzalez, J., Jr., Brown, B. J. and Carlton, B. C. (1982) *Proc. Natl. Acad. Sci. USA*, 79, 6951-6955). In the case of *B. thuringiensis* var. *israelensis*, two independent studies of strains cured of one or more plasmids concluded that delta-endotoxin synthesis is critically dependent on the presence of a 72-75 Md (ca 110 kb) plasmid (Ward, E. S. and Ellar, D. J. (1983) *FEBS Lett.*, 158, 45-49; Gonzalez, J. M., Jr. and Carlton, B. C. (1984) *Plasmid*, 11, 28-38). Using the newly discovered capacity of *B. thuringiensis* for plasmid transfer by a conjugation-like mechanism, authors in Gonzalez, J., Jr., Brown, B. J. and Carlton, B. C. (1982) *Proc. Natl. Acad. Sci. USA*, 79, 6951-6955) have shown that one or more plasmids in several *B. thuringiensis* strains code for the delta-endotoxin structural gene. However, to date, transfer of plasmids from *B. thuringiensis* var. *israelensis* to other *B. thuringiensis* serotypes has not been achieved (Gonzalez, J., Jr., Brown, B. J. and Carlton, B. C. (1982) *Proc. Natl. Acad. Sci. USA*, 79, 6951-6955) and it therefore remains possible that the 72-75 Md plasmid encodes a regulator of delta-endotoxin production, rather than the structural gene.

We describe the resolution of this question by the isolation from hhe purified 72-75 Md plasmid of a DNA fragment that includes the *israelensis* toxin gene that encodes for a protein toxin of about 27,340 Daltons, the complete nucleotide base sequence of the gene and the amino acid sequence of the protein expressed by the gene code and deduced from the nucleotide base sequence of the structural coding segment of the gene.

DESCRIPTION OF THE FIGURES

FIG. 3 Restriction endonuclease cleavage map of the portion of pIP174 containing the 27-kdal toxin gene, and whose sequence is given in FIG. 4(a).

The relative location of various restriction sites were determined as described in the specification. Sizes of each fragment are given in bases (b). It should be noted that the numbering on FIG. 3 refers only to the numbering on FIG. 4(a) and not to the numbering on FIG. 4(b). Thus, FIG. 4(a) and FIG. 3 refer to the sequence beginning at the second TaqI site on FIGS. 4(b) and 5(b).

FIG. 4(a) Complete base sequence for DNA sequence of gene obtained from *Bacillus thuringiensis* var. *israelensis* coding for the 27-kdal toxin having the amino acid sequence also set forth (top rows starting at about base number 297) in the FIG. 4 and which are explained in more detail below.

Figure 5B:
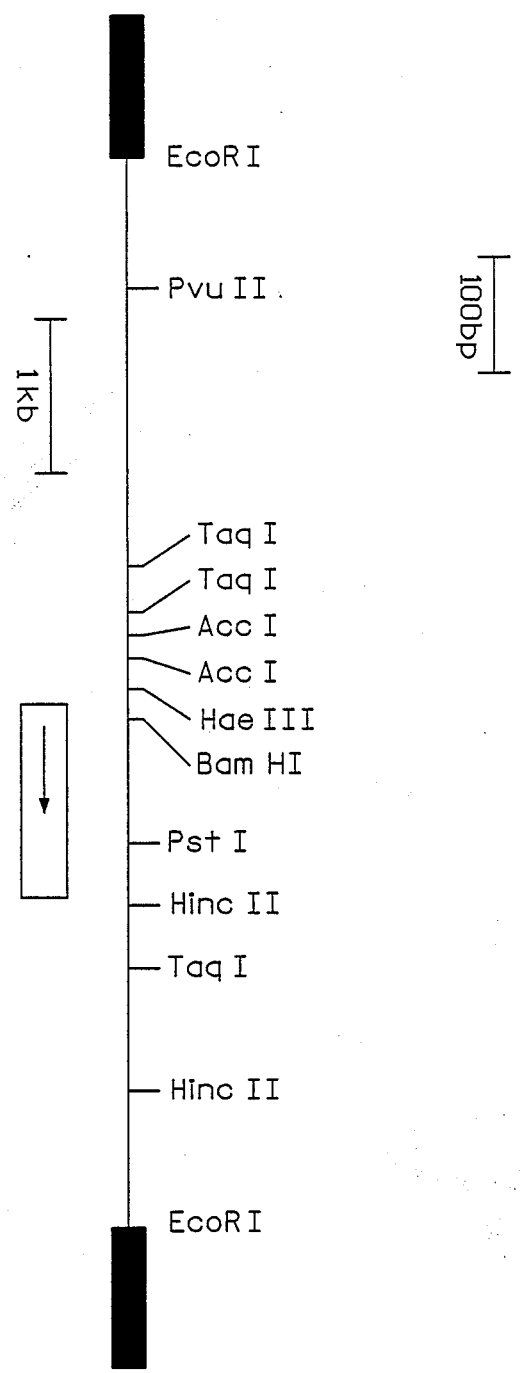

FIG. 4(b) Nucleotide sequence of 1408 bp of var. *israelensis* DNA encoding the 27-kdal toxin and extending from the TaqI site proximal to the PvUII site in FIG. 5(b) to the TaqI site beyond the 3' end of the toxin gene coding region. The amino acid sequence for the open reading frame from nucleotide 509-1256 is shown. Regions for the initiation sites for transcription used in *B. thuringiensis* var. *israelensis* and *E. coli*, determined by S1 nuclease mapping are indicated by PB1 (var. *israelensis*) and PB1, PEC1 (*E. coli*). In addition, there appears to be a third initiation site used in *E. coli* upstream of the AhaII site at nucleotide 92. This site has not been localized. A highly A+T rich region to the 5' side of PB1 is underlined.

FIG. 5(a) Circular plasmid pIP174 restriction endonuclease cleavage map. FIG. 5(b) Restriction endonuclease map of pIPECO 5. The single line represents var. *israelensis* DNA; the solid boxes represent pUC12 DNA. The location of the 27-kdal toxin gene is shown, with the direction of transcription indicated by an arrow.

Figure 5C:
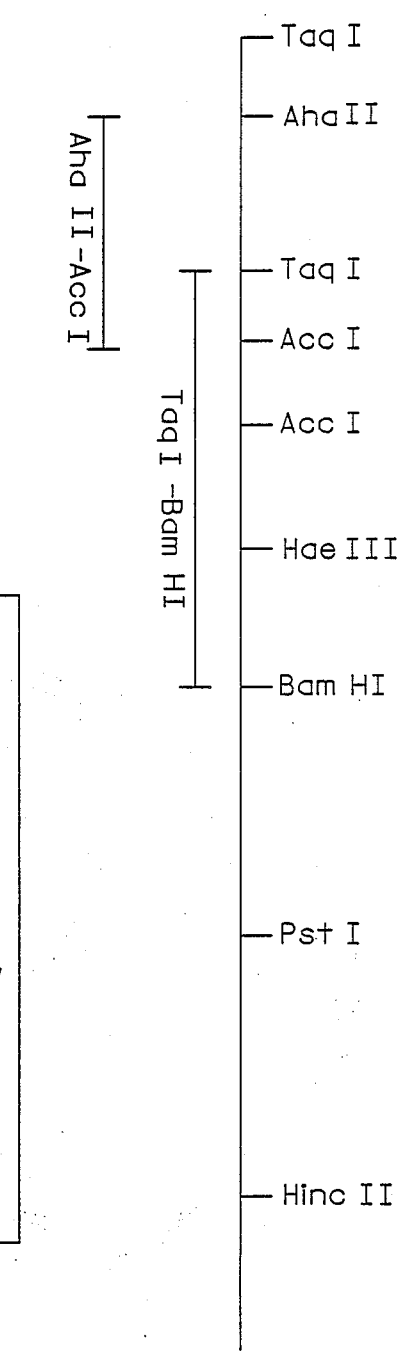

FIG. 5(c) DNA fragments used as probes in the S1 mapping experiments. The probes were made by the prime-cut method (materials and methods) using the appropriate M13 clones. Restriction enzyme cleavage sites are shown for each probe.

Figure 6:
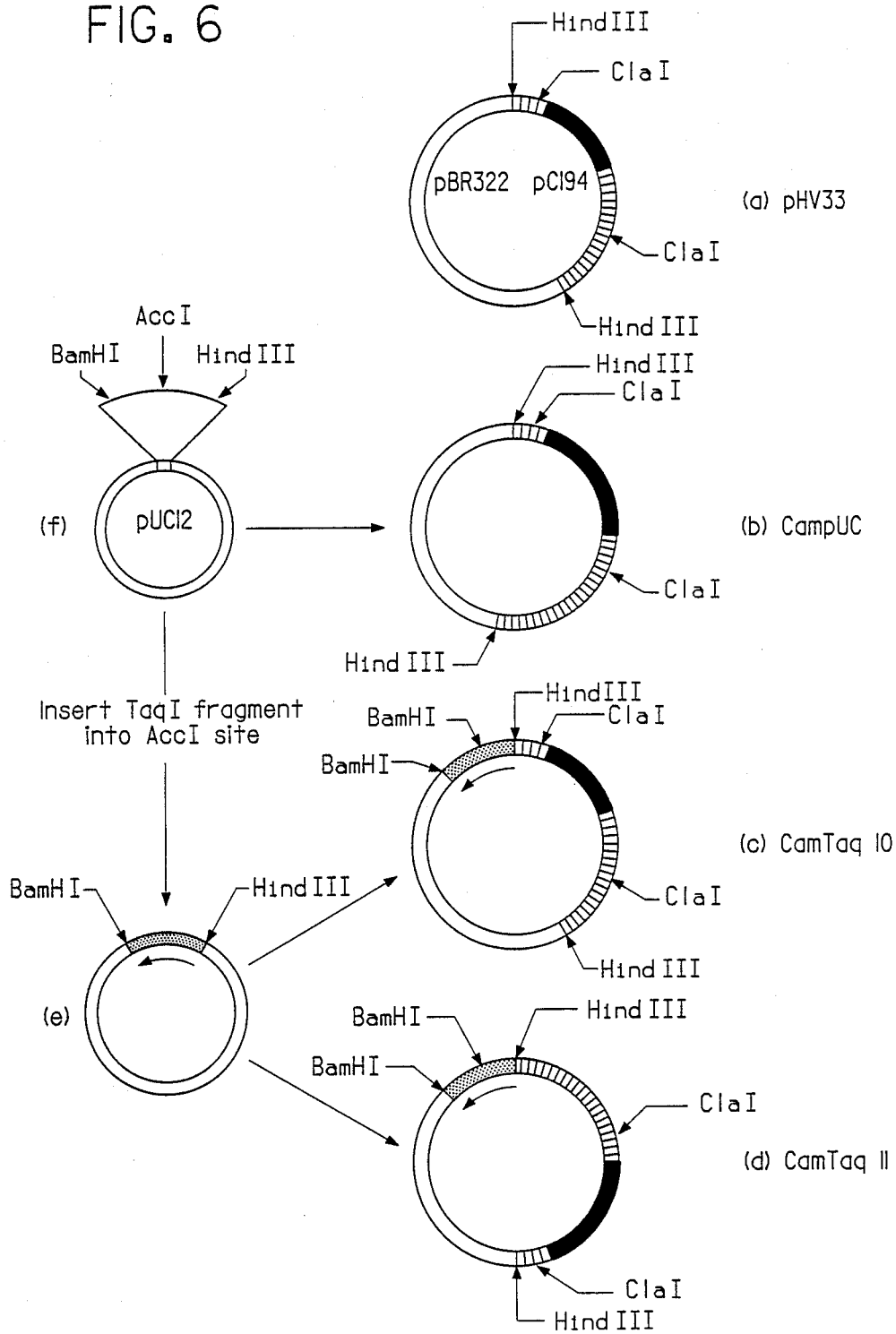
Figure 7:
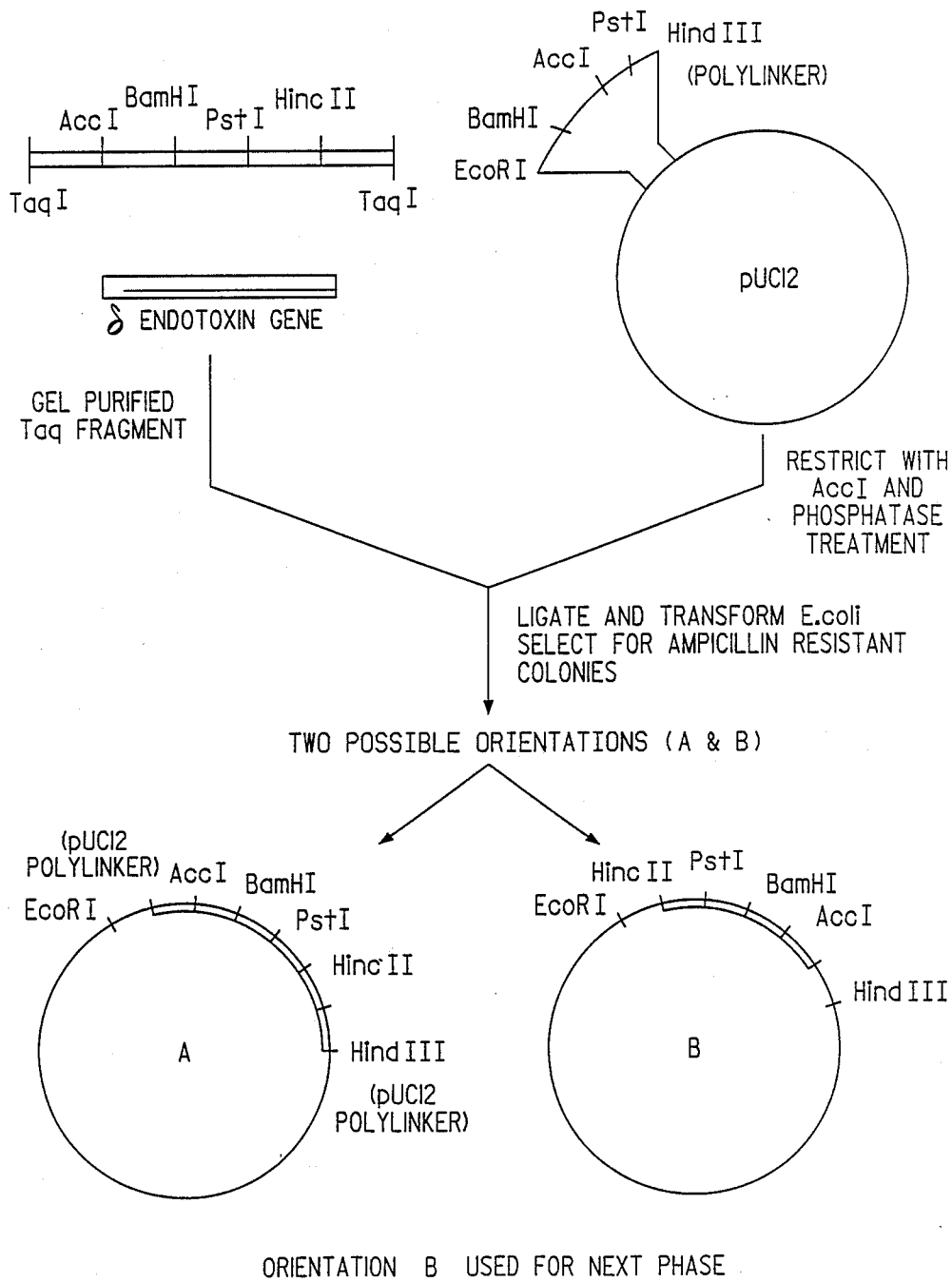
Figure 8:
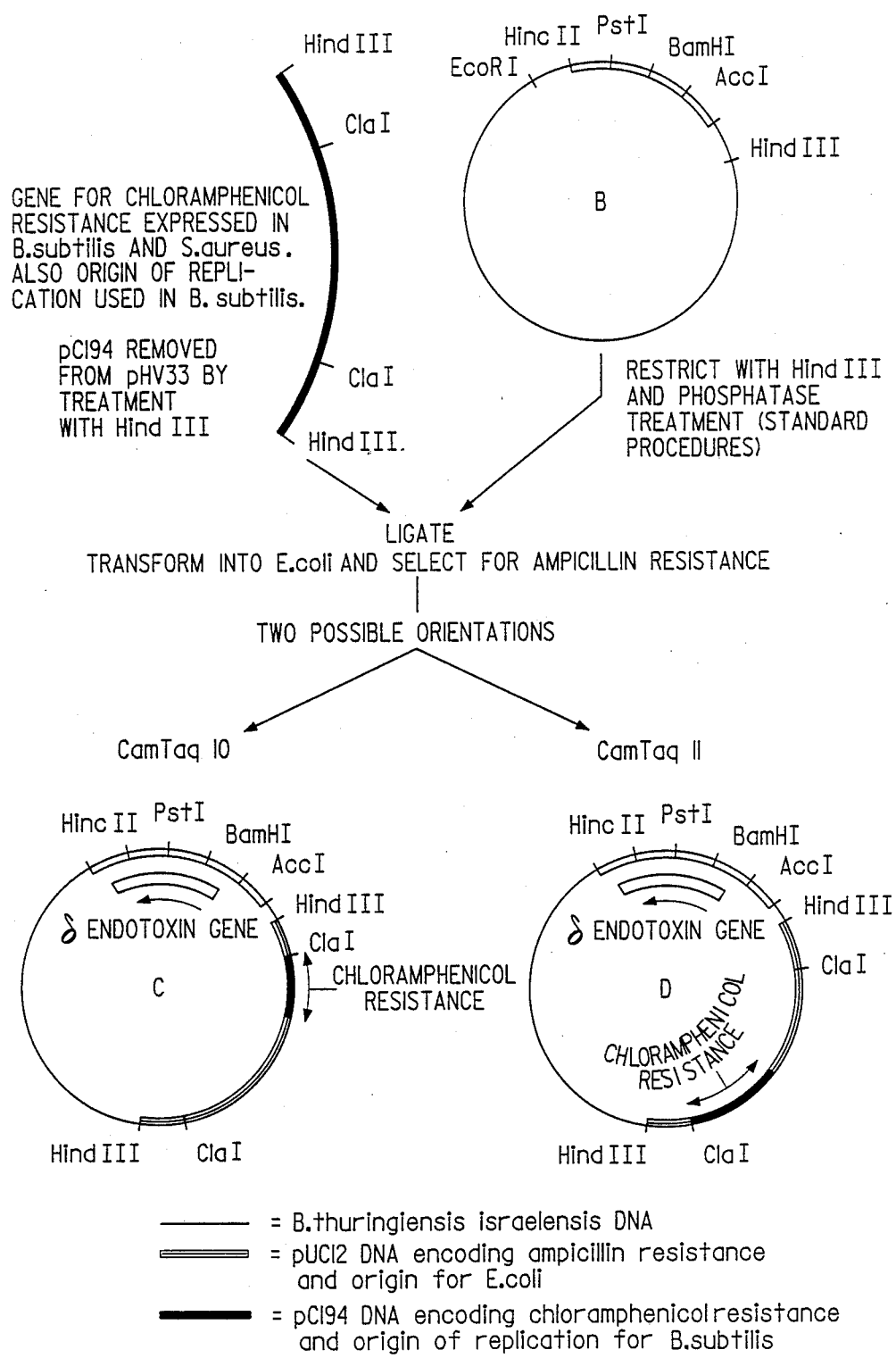

FIGS. 6, 7 and 8 pC194 DNA, was obtained by restricting the cloning vector pHV33 with HindIII (which yields pBR322 and pC194) and then purifying the 2.7 kb pC194 fragment by standard procedures.

--- pC194
Region of pC194 which confers chloramphenicol resistance in *B. subtilis*.
1.2-kb TaqI fragment from *B. thuringiensis* var. *israelensis* carrying the 27-kdal delta-endotoxin gene. The arrow shows the direction of transcription of the gene.

---

There is also a Bam H1 restriction site in the polylinker of pUC12 which needs to be considered when analyzing any restriction data for CamTaq 10 (FIG. 8, C) and CamTaq 11 (FIG. 8, D). In FIG. 8 the *B. thuringiensis* var. *israelensis* DNA used in constructing CamTaq 10 and CamTaq 11 was a 1.2 kb TaqI fragment. This was obtained by TaqI digestion of pIP173; the digest was electrophoresed in agarose by standard procedures and the 1.2 kb fragment recovered from the agarose by standard procedures.

Figure 9:
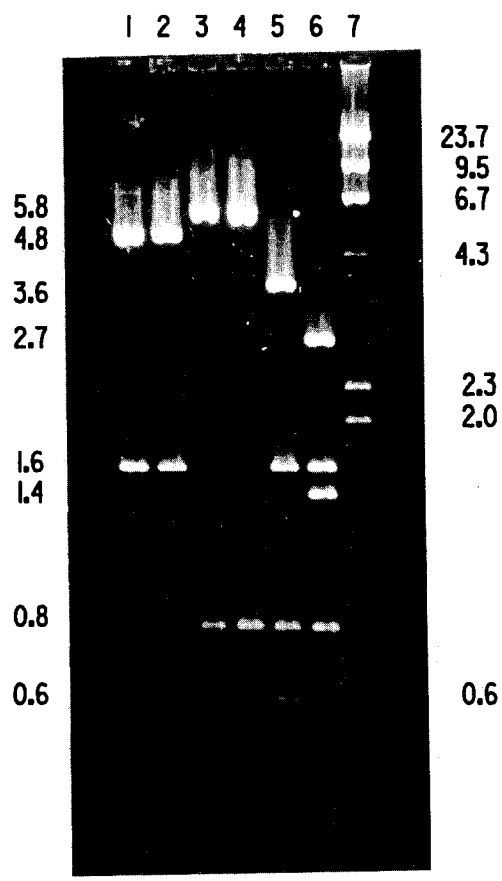

FIG. 9 Agarose gel electrophoresis of restriction enzyme digestion products of CamTaq 10 and CamTaq 11: ClaI digest of CamTaq 10 (lane 1); ClaI digest of CamTaq 11 (lane 2); BamHI digest of CamTaq 10 (lane 3); BamHI digest of CamTaq 11 (lane 4); BamHI-ClaI digest of CamTaq 10 (lane 5); BamHI-ClaI digest of CamTaq 11 (lane 6); HindIII digested lambda-DNA with fragment sizes marked in the right margin (in kb) (lane 7). Calculated sizes of restriction enzyme digestion products are marked in the left margin (in kb).

Figure 10:
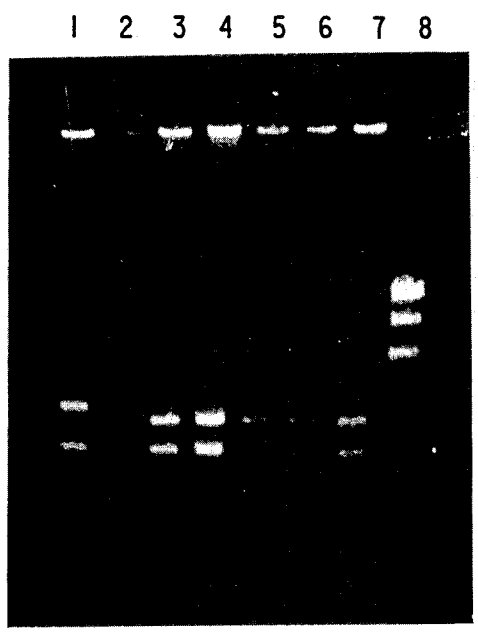
Figure 10:
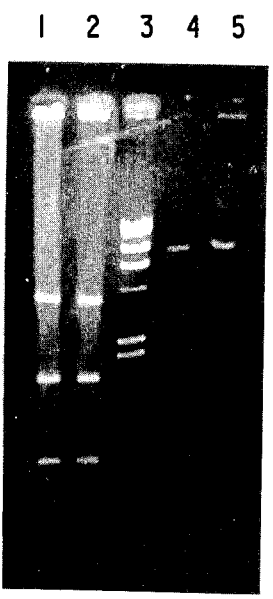

FIG. 10 Agarose gel electrophoresis of plasmids isolated from *B. subtilis* clones transformed with pHV33, CamTaq 10 or CamTaq 11.
(a) HindIII digested plasmid DNA isolated from *B. subtilis* 168 clones transformed with: pHV33 (lane 1); CamTaq 11 (lanes 3–5); CamTaq 10 (lanes 6 and 7); HindIII digested lambda-DNA (lane 8).
(b) Plasmid DNA isolated from 2 *B. subtilis* spoOJ clones transformed with CamTaq 10: undigested (lanes 4 and 5); digested with ClaI and BamHI (lanes 1 and 2); Hind III digested lambda-DNA (lane 3).

Figure 11:
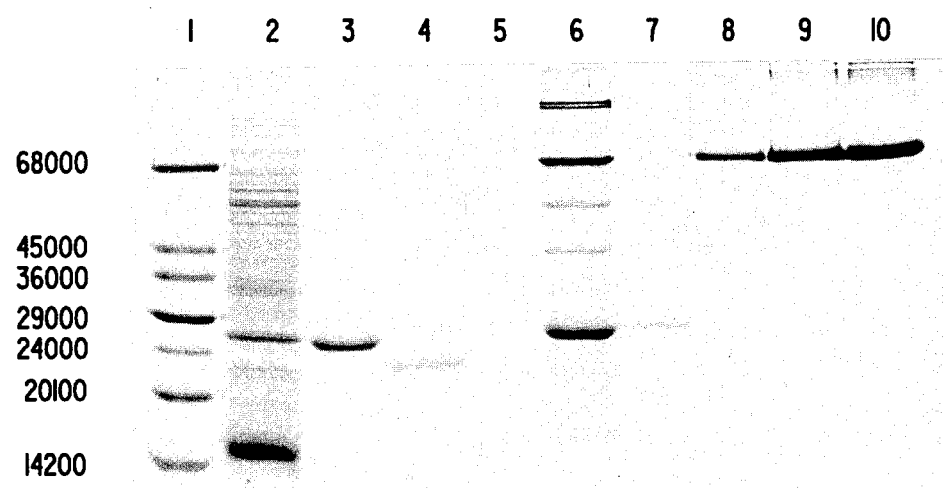

FIG. 11 SDS/13% polyacrylamide gel electrophoresis, Coomassie blue stained.

Lane 1, molecular weight standards: bovine albumin (68000 Da), egg albumin (45000 Da), glyceraldehyde-3-phosphate dehydrogenase (36000Da), carbonic anhydrase (29000 Da), trypsinogen (24000 Da), trypsin inhibitor (20100 Da), alpha-lactalbumin (14200 Da); lane 2, 50 microliters crude protein extract from CT 11-2 sporulating cells; lane 3, 35 microliters crystal preparation from CT 11-2 (*B. subtilis*); lane 4, CT 11-2 soluble crystal protein and lane 5, CT 11-2 insoluble crystal protein obtained by incubation of 25 micro liters CT 11-2 crystal preparation in 50 mM Na$_2$CO$_3$ (pH 10.5); lane 6, 70 micrograms native *B. thuringiensis* var. *israelensis* crystal delta-endotoxin; lane 7, var. *israelensis* soluble crystal protein obtained by incubation of 15 micrograms native crystal toxin in 50 mM Na$_2$CO$_3$-HCl (pH 10.5); lane 8, 3.1 micrograms bovine serum albumin; lane 9, 6.25 micrograms bovine serum albumin; lane 10, 12.5 micrograms bovine serum albumin.

Figure 12:
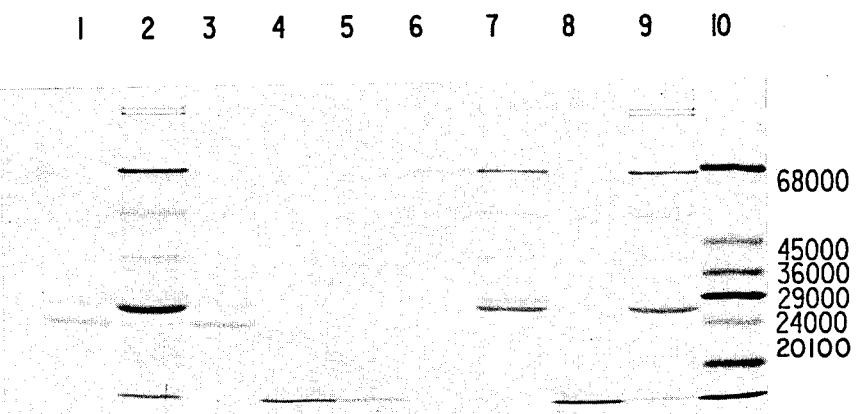
Figure 12:
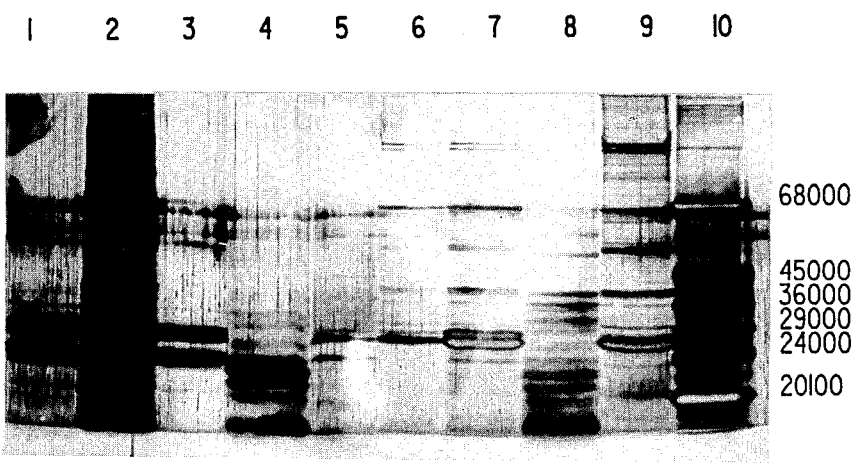

FIG. 12 SDS/13% polyacrylamide gel electrophoresis, Coomassie Blue stained (a), and silver stained (b). Lanes 1 and 3, *B. subtilis* CT 11-2 soluble crystal protein obtained by incubation of 35 microliters crystal preparation in 50 mM Na$_2$CO$_3$-HCl (pH 10.5); lane 2, var. *israelensis* soluble crystal protein obtained by incubation of 30 micrograms native crystal deltaendotoxin in 50 mM Na$_2$CO$_3$-HCl (pH 10.5) with *B. subtilis* CT 11-2 cells present; lane 4, approximately 2.5 micrograms solubilized CT 11-2 crystal preparation treated with gut extract from *Aedes* larvae; lane 5, CT 11-2 insoluble crystal protein from 50 microliters crystal preparation; lane 6, var. *israelensis* insoluble crystal protein and lane 7, var. *israelensis* soluble crystal protein from 30 micrograms native crystal delta-endotoxin; lane 8, 30 micrograms solubilized var. *israelensis* crystal protein treated with gut extract from *Aedes* larvae; lane 9, 30 micrograms native *B. thuringiensis* var. *israelensis* crystal delta-endotoxin; lane 10, molecular weight standards, as in FIG. 11.

SUMMARY OF THE INVENTION

The present invention is directed to a DNA composition having the nucleotide base sequence coding for an expressible protein toxin having a molecular weight of about 27,340 Daltons, or an insecticidally effective segment thereof, substantially homologous with a reported 26,000-28,000 Da protein present in the crystal of *Bacillus thuringiensis* var. *israelensis* having insecticidal properties, microorganisms transformed with such DNA, insecticidal compositions containing an insecticidally effective amount of the protein toxin or transformed microorganisms and to use of said compositions for control of insects, such as Diptera, and especially larvae thereof. The literature has previously described as either a 26,000 or 28,000 Da delta-endotoxin has now been established by the present inventors to be a protein of about 27,340 Da and the invention is directed to the gene coding for that 27,340 Da protein, which had been less accurately identified in the literature. Thus, antisera or antibodies said to be raised to a 26,000 or 28,000 Da protein of the literature are based upon the less accurate identifications of the literature prior to the current 27,340 Dalton determination of the protein in the present invention. In this application-reference to the 27,340 Da protein has often been abbreviated as 27-kdal for convenience.

One embodiment of the invention comprises a method of synthesizing within a microorganism (e.g. bacterial) host and expressing a selected (mature) protein or polypeptide segment thereof, having insecticidal activity, which comprises culturing the (bacterial) host, the (bacterial) host being transformed with a cloning vehicle or vector comprising a plasmid or DNA composition having a nucleotide base sequence described herein or a segment thereof coding for an insecticidally effective polypeptide.

Thus, a microorganism, such as a (bacterial) host, is transformed by introducing thereinto a heterologous DNA composition coded in a plasmid or a DNA composition having the nucleotide base sequence described herein and capable of being both transcribed and expressed in said microorganism. Preferably, the bacterial host into which the (recombinant) plasmid or heterologous DNA composition (sequence) is introduced is *E. coli* or a *Bacillus* strain (such as *B. megaterium* or *B. subtilis,* etc.) or the like.

The invention also includes a vector comprising an ability to transform a transformable microorganism and an insert including a DNA composition hybridizable with a gene segment for a protein present in a crystal of *Bacillus thuringiensis;* preferably, the DNA composition (sequence) is hybridizable with a gene, or segment thereof, coding for an expressible protein present in a crystal of *Bacillus thuringiensis* var. *israelensis* and is capable of transforming a bacterial host, such as *E. coli,* a *Bacillus* strain (such as *B. megaterium* or *B. subtilis,* etc.) or the like.

For example, this includes a plasmid having the capability of replication in a bacterial host species containing an expressible heterologous DNA composition coding for a 27-kdal protein toxin or insecticidally effective segment thereof and including an expression mechanism for said heterologous DNA that is recognized by the host species system but does not exhibit substantial growth phase limitations in the bacterial host species. Such a plasmid is prepared by (1) isolating from a crystal protein-producing strain of *Bacillus thuringiensis* a first fragment of DNA comprising an expressible heterologous DNA composition having a nucleotide base sequence coding for the 27-kdal protein toxin, (2) providing one or more other DNA fragments that contribute(s) an expression mechanism for heterologous DNA in a selected bacterial host other than B. *thuringiensis,* the expression mechanism being recognized by said host without exhibiting substantial growth phase limitations, and (3) ligating said first DNA fragment and said other fragment(s) in the correct arrangement for expression of the heterologous protein-producing DNA coding in said host. For example, the DNA composition has substantial sequence homology to plasmid pIP173 or pIP174 or a segment thereof that codes for a 27-kdal protein toxin, such as the base sequence of FIG. 3, section C to B or A to B, FIG. 4(*a*), base pair numbers from about 1-1045 or 296 to 1045, or FIG. 4(*b*), base pair numbers from about 1 to 1408 or 509 to 1258. (It should be noted that the numbering on FIG. 3 refers only to the numbering on FIG. 4(*a*) and not to the numbering on FIG. 4(*b*). Thus, FIG. 4(*a*) and FIG. 3 refer to a sequence beginning at the second TaqI site on FIGS. 4(*b*) and 5(*b*).)

The present invention further includes: (1) An essentially pure recombinant (circular) plasmid having an insecticidal 27-kdal protein toxin gene, or segment thereof, from *Bacillus thuringiensis* var. *israelensis* characterized by a molecular size of approximately 1045 bases or nucleotides and a restriction endonuclease cleavage map as shown in FIG. 5(*a*), sections C to B; (2) an essentially linearized plasmid DNA composition having an insecticidal 27-kdal protein toxin gene, or segment thereof, coding for an expressible protein substantially homologous to a protein present in a crystal from *Bacillus thuringiensis* var. *israelensis,* said gene characterized by a molecular size of approximately 1408 or 1045 bases or nucleotides (FIG. 4(*b*)) or a restriction endonuclease cleavage map as shown in FIG. 3, sections from C to B; and (3) a plasmid DNA composition having an insecticidal protein structural DNA gene segment, from *Bacillus thuringiensis* characterized by a molecular size of approximately 750 bases or nucleotides and a restriction endonuclease cleavage map as shown in FIG. 3, sections A to B, FIG. 4(*a*), base pair numbers 295 to 1045, or FIG. 4(*b*), base pair numbers 509 to 1258.

More particularly, the present invention is directed to a recombinant plasmid comprising a heterologous DNA composition having a nucleotide base sequence having substantial sequence homology to a DNA segment coding for a 27-kdal protein present in a crystal of *Bacillus thuringiensis* var. *israelensis,* which said plasmid is capable of replicating in a microorganism host, and comprising with reference to FIGS. 3 or 4(*a*) (A) an expression mechanism including (1) a translational start signal (296), e.g. ATGGAA, no more than approximately 95 nucleotides upstream from a Bam HI restriction site (393), (2) a ribosome binding site (257), e.g. AAGGA, preceding the translational start signal by approximately 11 nucleotides, and (3) a promoter region preceding the translational start signal by up to about 295 nucleotides (e.g. about 220 to 226 and/or 240 to 246) and (B) a structural DNA gene segment that is an Open Reading Frame (ORF) continuing unbroken about 90 nucleotides beyond a Hinc II restriction site (952) ending with a stop codon (1045), e.g. TAA. One or more transcription starting sites in the promoter region can precede the ribosome binding site. For example, this DNA composition sequence is homologous to a DNA segment coding for a protein present in a crystal of *Bacillus thuringiensis* var. *israelensis* and is capable of expression in a microorganism (bacterial) host, such as *E. coli* or a *Bacillus* strain (such as *B. megaterium* or *B. subtilis,* etc.) or the like.

The invention also includes a method for identifying a gene capable of expressing a (27-kdal) protein toxin that comprises (1) hybridizing a probe consisting essentially of labeled DNA, or RNA complementary to a DNA segment from a 750 base segment of DNA obtained from *Bacillus thuringiensis* var. *israelensis* shown in FIGS. 3 or 4(*a*) or (*b*), with a (27-kdal) protein toxin gene source; (2) selecting exogenous DNA segments from said gene source that hybridize with said probe; (3) forming a recombinant DNA vector from said exogenous DNA segments and a vector; (4) transforming a host microorganism with said recombinant DNA vector; and (5) selecting transformed microorganisms that express a (27-kdal) protein toxin.

The present invention also contemplates and includes: (1) spores produced by microorganisms containing a DNA composition described herein. (2) an insecticidal composition comprising a microorganism, a lyophilizate or other preservation form of a microorganism containing such a plasmid or DNA composition. For example, such a composition, upon dilution with water, or growth medium produces a culture medium of the microorganism suitable for germination of said spores. Also included in the invention is a protein toxin of about 27,340 Daltons, which has been produced by a microorganism containing (coded in) such a plasmid or DNA sequence described herein, and an insecticidal composition comprising a 27-kdal protein toxin produced by a microorganism containing such a DNA composition, which protein is substantially homologous with a protein present in the crystal from *Bacillus thuringiensis* var. *israelensis*.

(3) a method of controlling insects at a locus comprising applying to the insects or to the locus an insecticidally effective amount of a microorganism or 27-kdal protein toxin thereof produced by a microorganism containing a recombinant plasmid or heterologous DNA composition thereof, including a method wherein the insects are in the larvae stage.

(4) the 27-kdal protein, per se, or a toxic segment thereof, including a 24-25 kdal segment or smaller segment, which is toxic to insects. Such segments can be produced by protease digestion or direct peptide synthesis methods known to those skilled in the art.

The invention is described in more detail below.

Materials

Bacterial strains and plasmids

The strains used were: a derivative of *B. thuringiensis* var. *israelensis* IPS78, Collection of Institute Pasteur, Paris, France, deposit number 14-1, that had been cured of several plasmids present in the wild-type strain but containing extractable 72-75 Md plasmid (Ward, E. S. and Ellar, D. J. (1983) *FEBS Lett.*, 158, 45–49); *Escherichia coli* JM101 American Type Culture Collection, Rockville, Md., deposit number ATCC 33876 and plasmid pUC12 have been described previously (Messing, J. (1983) *Methods Enzymol.*, 101, 20–78). *Bacillus subtilis* 168, deposited as number 1A1 in the Bacillus Genetic Stock Centre, Columbus, Ohio, and *Bacillus subtilis* non-sporulating mutant spoOJ87; number IS27 in the *Bacillus* Genetic Stock Centre collection, Columbus, Ohio, and are all publicly available. In addition to the above public deposits, the *E. coli*, *B. thuringiensis* var. *israelensis* IPS78, *B. subtilis* 168 and *B. subtilis* spoOJ87 have also been placed in deposit under the Budapest Treaty at National Collection of Industrial Bacteria, Torry Research Station, Aberdeen, Scotland, as deposit numbers NCIB12110, NCIB12109, NCIB12107, and NCIB12108, respectively. Other strains or microorganisms having substantially the same characteristics for cloning can be used.

Illustrative Embodiments and Methods

The following embodiments are presented for the purpose of illustrating the processes and products of the present invention, but should not be regarded as limiting the invention in any way.

Isolation of plasmid DNA pUC12 plasmid was prepared from *E. coli* JM101 by a lysozyme-detergent lysis method (Maniatis, T., Fritsch, E. F. and Sambrook, J. (1982) in: "Molecular Cloning. A Laboratory Manual", Cold Spring Harbor Laboratory, N.Y.) with the following modifications: (i) Triton X-100 was used to a final concentration of 1% instead of sodium dodecyl sulfate (SDS); (ii) NaCl was omitted after Triton addition. Total plasmid DNA from *B. thuringiensis* var. *israelensis* was prepared by the method of Casse, F., Boucher, C., Julliott, J. S., Michel, M. and Denairie, J. (1979) *J. Gen. Microb.*, 113, 229–242. The 72-75 Md plasmid was subsequently purified from total plasmid DNA by preparative vertical electrophoresis on 3 mm thick 0.5% low gelling temperature agarose slabs (Seaplaque, FMC Colloids). Gel bands were visualized and excised as previously described (Weislander, L. (1979) *Anal. Biochem.*, 98, 305–309; Burns, D. M. and Beacham, I. R. (1983) *Anal. Biochem.*, 135, 48–51). Plasmid DNA from excised bands was purified by phenol/chloroform extraction and ethanol precipitation. Total CCC DNA for use in the in vitro transcription-translation system was purified on caesium chloride gradients as in Maniatis, T., Fritsch, E. F. and Sambrook, J. (1982) in "Molecular Cloning. A Laboratory Manual", Cold Spring Harbor Laboratory, N.Y.

The 72 Md plasmid of *B. thuringiensis* var. *israelensis* was purified from total plasmid DNA by preparative vertical electrophoresis on 3 mm thick 0.5% low gelling temperature agarose slabs (Seaplaque, FMC Colloids). Gel bands were visualzed and excised as previously described by Weislander (1979). Plasmid DNA from excised bands was purified by phenol/chloroform extraction and ethanol precipitation.

Cloning of DNA

Vector (pUC12) and *B. thuringiensis* var. *israelensis* IPS78 DNA (72-75 Md plasmid) was digested to completion with HindIII (New England Biolabs). The medium salt buffer of Maniatis, T., Fritsch, E. F. and Sambrook, J. (1982) in "Molecular Cloning. A Laboratory Manual", Cold Spring Harbor Laboratory, N.Y., was used for HindIII digestions, except that for DNA extracted from low gelling temperature agarose, bovine serum albumin (Sigma) was added to a final concentration of 100 micrograms/ml$^{-1}$. 25 ng restricted vector and 100 ng restricted 72-75 Md plasmid from *B. thuringiensis* var. *israelensis* IPS78 were ligated with T4 DNA ligase (New England Biolabs) at 15° C. for 16 hr, using the manufacturer's instructions for buffer, except that bovine serum albumin was used at a final concentration of 100 micrograms/ml$^{-1}$ (Burns, D. M. and Beacham, I. R. (1983) *Anal. Biochem.*, 135, 48–51). Portions of the ligation mix were used to transform *E. coli* JM101 (Hanahan, D. (1983) *J. Mol. Biol.*, 166, 557–580) and transformants were selected on L agar (Maniatis, T., Fritsch, E. F. and Sambrook, J. (1982) in "Molecular Cloning. A Laboratory Manual", Cold Spring Harbor Laboratory, N.Y.) containing 170 micrograms/ml$^{-1}$ ampicillin.

Preparation of polyclonal antibodies

The protein delta-endotoxin (previous literature values 26,000–28,000 Da) was isolated from purified crystals of *B. thuringiensis* var. *israelensis* by conventional preparative gel electrophoresis. Purified delta-endotoxin was mixed with Freunds complete adjuvant and polyclonal antibodies were raised by subcutaneous injection of this material into New Zealand White rabbits. Specificity of antibodies was confirmed by Western blotting of protein preparations electrophoretically transferred to nitrocellulose from SDS polyacrylamide gels (Towbin, H., Staehlin, T. and Gordon, J. (1979) *Proc. Natl. Acad. Sci. USA*, 76, 4350–4354) using horseradish peroxidase-conjugated anti-rabbit immunoglobulin (Sigma) to detect bound antibody (Hawkes, R., Niday, E. and Gordon, J. (1982) *Anal. Biochem.*, 119, 142–147).

Analysis of recombinants

Recombinant clones were analyzed using an in vitro transcription-translation system (Howe, C. J., Bowman, C. M., Dyer, T. A. and Gray, J. C. (1982) *Mol. Gen. Genet.*, 186, 525–530). DNA from individual recombinants or recombinant groups was extracted using a small-scale lysozyme-Triton plasmid preparation method (Maniatis, T., Fritsch, E. F. and Sambrook, J. (1982) in "Molecular Cloning. A Laboratory Manual", Cold Spring Harbor Laboratory, N.Y., and J. Karn, personal communication) and up to 5 micrograms DNA was added to the *E. coli* system. Products from the in vitro system were analyzed using 13% acrylamide gels (Laemmli, U. K. (1970) *Nature*, 227, 680–685) and fluorography (Chamberlain, J. P. (1979) *Anal. Biochem.*, 98, 131–135).

Figure 1:
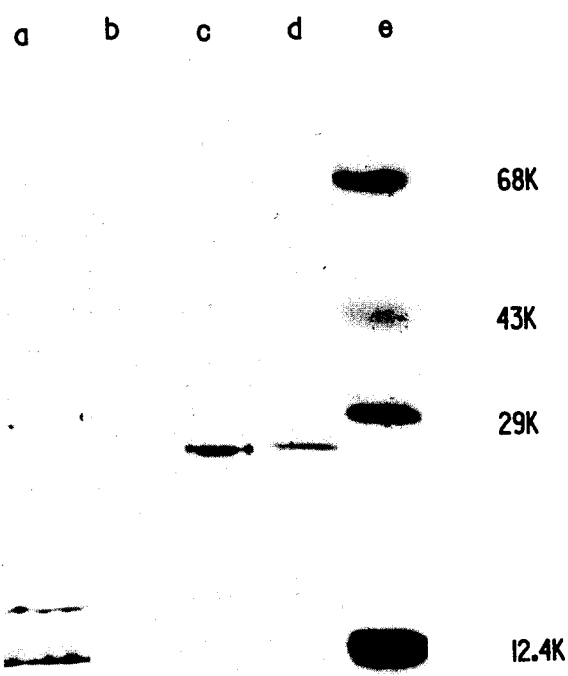
FIG. 1 Fluorographs of SDS 13% polyacrylamide gels of the $^{35}$S-labelled polypeptides synthesized in the *E. coli* transcription-translation system primed with either HindIII digested total *B. thuringiensis* var. *israelensis* plasmid DNA, or plasmid pIP174 DNA, and : supplemented with L-[$^{35}$S]methionine: Lane (a), total products from pIP174 DNA; lane (b), material precipitated from the products shown in lane (a) by addition of preimmune serum; lane (c), material precipitated from (a) by addition of antibody raised against the 27000 Da authentic *israelensis* delta-endotoxin; lane (d), material precipitated by antibody against the 27000 Da authentic *israelensis* delta-endotoxin from the *E. coli* transcription-translation system primed with HindIII digested total *B. thuringiensis* var. *israelensis* plasmid DNA; lane (e), molecular weight standards labeled with ethyl-[1-$^{14}$C]acetimidate hydrochloride (Howe, C. J., Bowman, C. M., Dyer, T. A. and Gray, J. C. (1982) *Mol. Gen. Genet.*, 186, 525-530).

Preliminary screening with restriction enzymes showed that when HindIII digested *B. thuringiensis* var. *israelensis* total plasmid DNA was added to the *E. coli* in vitro transcription-translation system, a single polypeptide having a molecular weight within the range of the 26,000–28,000 Da natural *israelensis* toxin was precipitated by polyclonal antibodies raised to the purified 6,000–28,000 Da delta-endotoxin (FIG. 1). HindIII was therefore used to digest the purified 72–75 Md plasmid of IPS78 and the products ligated into HindIII digested pUC12 as described above. A library of 450 colonies was selected after transformation of *E. coli* JM101 with the ligation mixture. Random analysis of 60 colonies from this library showed that 77% (46) were recombinants.

Plasmid DNA was then extracted from three groups of 150 clones and 5 micrograms DNA from each group added to the in vitro transcription-translation system. All three pools contained recombinant(s) that synthesized a 27-kdal polypeptide precipitable by the 26,000–28,000 Da protein toxin polyclonal antibodies. The group containing the most 27-kdal protein detectable by immunoprecipitation was further subdivided using the *E. coli* in vitro system. DNA was isolated from groups of 25, then 5 and finally single recombinant clones and screened for toxin synthesis. In this way, two toxin-coding recombinants, pIP173 and pIP174, were identified from one of the groups of five clones (FIG. 1) and used for subsequent analysis.

The plasmid pIP174 demonstrated evidence that it is a recombinant plasmid consisting of vector and target the *Bacillus thuringiensis* var. *israelensis* 27-kdal protein gene DNA. FIG. 1 shows fluorographs of sodium dodecyl sulfate 13% polyacrylamide gels of $^{35}S$-labeled polypeptides synthesized in the *E. coli* transcription-translation system primed with either HindIII digested total *B. thuringiensis* var. *israelensis* plasmid DNA, or plasmid pIP174 DNA and supplemented with L-[$^{35}S$]methionine: Lane (a), total products from pIP174 DNA; lane (b), material precipitated from (a) by addition of preimmune serum; lane (c), material precipitated from (a) by addition of polyclonal antibodies raised against the 26,000–28,000 Da natural *israelensis* delta-endotoxin; lane (d), material precipitated by polyclonal antibodies raised against the 26,000–28,000 Da natural *israelensis* deltaendotoxin from the *E. coli* transcription-translation system primed with HindIII digested total *B. thuringiensis* var. *israelensis* plasmid DNA; lane (e), molecular weight standards labeled with ethyl-[1-$^{14}C$]acetimidate hydrochloride. Lane (c) in FIG. 1 shows that when the plasmid DNA extracted from recombinant cells harboring pIP174 is used to direct synthesis of polypeptides in an *E. coli* in vitro transcription-translation system, a polypeptide antigen is made that can be immunoprecipitated using polyclonal antibodies made against the 26,000–28,000 molecular weight natural delta-endotoxin present in the crystal from *B. thuringiensis* var. *israelensis*. This polypeptide was not detected when preimmune serum was substituted for anti-27-kdal toxin antibodies (lane (b)).

Figure 2:
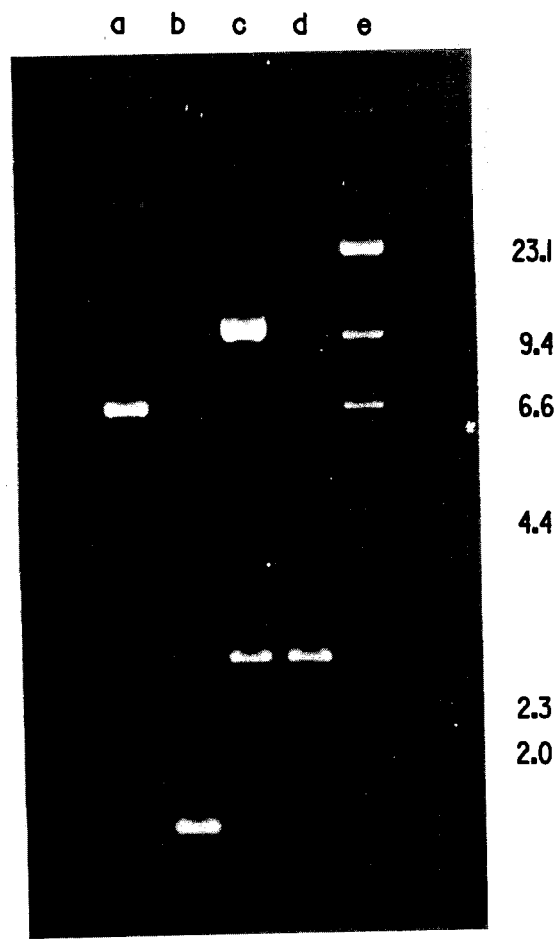
FIG. 2 Agarose gel electrophoresis of covalent closed circular forms of pIP174, pUC12 and their HindIII digestion products: lane (a), pIP174 (covalent closed circular form); lane (b), pUC12 (covalent closed circular form); lane (c), HindIII digested pIP174; lane (d), HindIII digested pUC12; lane (e), HindIII digested lambda-DNA with fragment sizes on the right margin (in kb).

A recombinant plasmid of the invention, designated pIP174, is shown in FIG. 2. This figure shows agarose gel electrophoresis of covalent closed circular forms of pIP174, pUC12 and their HindIII digestion products: lane (a), pIP174 (covalent closed circular form); lane (b), pUC12 (covalent closed circular form); lane (c), HindIII digested pIP174; lane (d), HindIII digested pUC12; lane (e), HindIII digested lambda-DNA with fragment sizes on the right margin (in kb). By means of this gel analysis the recombinant plasmid (lane c) may be compared with pUC12, (lane d). After digestion by the enzyme HindIII, which excises the insert from the vector pUC12 DNA, the linearized pUC12 plasmid and the insert DNA have mobilities corresponding to molecular weights of $2.7 \times 10^6$ and $9.7 \times 10^6$ respectively, when compared with HindIII digested lambda-DNA (lane e). Molecular weights are the numbers shown on the right of FIG. 1 $\times 10^{-6}$ and refer to the HindIII digest of lambda-DNA. Identical results were obtained with HindIII digested pIP173. Thus, pIP173 and pIP174 are essentially identical plasmids.

In constructing recombinant plasmids according to the invention and in nucleotide sequence determination of the 27-kdal toxin gene, the following detailed procedures were employed. These procedures are given only by way of example and are not intended to limit the scope of the claims here.

Restriction analysis

The 9.7 kb insert DNA in the recombinant pIP174 contains the following sites for restriction enzymes in the order: Eco Rl, Pvu II, TaqI, Acc I, Bam HI, Pst I, Hinc II, TaqI, Hinc II, Eco Rl. As a result, a restriction map of the 27-kdal toxin gene from *Bacillus thuringiensis* var. *israelensis* was drawn up as shown in FIG. 3.

When pIP174 DNA restricted by either Pst I, Bam HI, or Hinc II is used to prime protein synthesis in the in vitro *E. coli* system, a polypeptide product of molecular weight 27-kdal immunoprecipable by anti-toxin antibodies is not made. The most likely explanation for these results is that Pst I, Bam HI and Hinc II have sites within, or very close to, the 27-kdal toxin gene.

DNA sequencing

To determine the nucleotide sequence of the 27-kdal toxin gene, selected restriction fragments of pIP174 generated by using enzymes known to have sites in and around the gene, were used. Therefore, fragments varying in length from 240 to 700 bp generated by using Pst I, Bam HI, Hinc II, TaqI, and Acc I were cloned in the sequencing vector M13mp8, Messing, J. (1983) Methods in Enzymology, 101, 20–78, and sequenced using the dideoxynucleotide method of DNA sequence determination Sanger, F., Nicklen, S. and Coulson, A. R. (1977) *Proc. Natl. Acad. Sci. USA*, 74, 5463–5467. From this sequence an Open Reading Frame (ORF) encoding a protein of molecular weight 27,340 was found. In the other 5 reading frames, multiple translational stop codons were found. The sequence of the 27-kdal toxin structural gene was determined for both the coding and non-coding strands of DNA. By way of illustration, the restriction map of a 5.4 kb EcoRI restriction fragment, derived from the 9.7 kb HindIII insert of pIP173, with the location of the protein toxin gene, is shown in FIG. 5(b). DNA extracted from a subclone consisting of the 4.6 kb PvuII-EcoRI fragment inserted into the cloning vector pUC12 produces a 27-kdal protein toxin when used to prime protein synthesis in the in vitro E. coli system. However, when DNA from a subclone derived from the 3.3 kb PvuII-HincII fragment is used in the in vitro system, a polypeptide product of a slightly lower, or higher, molecular weight than 27-kdal protein immunoprecipitated, the size of the polypeptide being dependent on the orientation of the insert in the vector. The most likely explanation for these findings is that HincII cuts at or very close to the carboxy terminus of the protein toxin gene. The restriction fragments derived from the subclone containing the 3.3 kb PvuII-HincII fragment, or from pIP173, were isolated and cloned into the sequencing vectors M13mp8 and M13mp9. The nucleotide sequence shown in FIG. 4(b) contains an extended open reading frame (ORF) starting at nucleotide 509 and ending at the termination codon TAA at position 1256. This ORF encodes a polypeptide of 249 residues, molecular weight 27,340. There are extensive hydrophobic regions throughout the protein.

The DNA composition having a nucleotide base sequence of the toxin gene is substantially as set forth in FIGS. 3 or 4(a) or (b). In FIGS. 4(a) and (b), the nucleotides (bottom rows) and amino acids (top rows beginning at about base 297, FIG. 4(a)) are identified by the single letter codes conventionally used in chemistry and molecular biology. Particular attention is called to a structural DNA composition having a nucleotide base sequence of the approximately 750 base segment of the gene for the 27-kdal protein toxin from *B. thuringiensis* substantially as set forth in FIG. 3, section A to B or FIG. 4(a), base pair position numbers from 295 to about 1045. Also, particular attention is also called to the DNA composition (sequence) containing about 1408 bases or a 750 base structural coding composition or segment thereof (1) for production of a cloning vehicle characterized by its ability to transform transformable non-sporulating or spore-forming microorganisms and by the fact that it contains an insert including a structural coding DNA composition or segment thereof of a gene coding for an insecticidal (crystal) protein, or (2) for the production of recombinant plasmids characterized by a DNA composition sequence (a) or (b) containing all of or only some of the following sites in the order shown: (a) TaqI-TaqI-AccI-AccI-HaeIII-BamHI-PstI-HincII-TaqI or (b) AccI, BamHI, PstI, HincII, such a sequence being hybridizable with a plasmid containing a segment of (crystal) protein gene from *Bacillus thuringiensis* var. *israelensis.*

It is noted that minor variations in the plasmid or DNA composition, the nucleotide base sequence of the gene or codons or alternate coding for the same or substantially equivalent amino acids which result in substantially the same expressed 27-kdal protein toxin are within the scope of the present invention. Thus, the invention includes a DNA composition (sequence) containing approximately 1408 bases of the gene (FIG. 4(*b*)) or the 750 bases of structural DNA and coding for a protein toxin having an amino acid sequence substantially as set forth in FIG. 3, section C to B or A to B, FIG. 4(*a*), base pair numbers from about 1-1045 or 296 to 1045 or FIG. 4(*b*), base pair numbers from about 1 to 1408 or 509 to 1258.

Location of the transcriptional start points for one protein toxin gene

*B. thuringiensis* var. *israelensis* cells grown overnight at 30° C. in PWYE (peptone/water/yeast extract) were diluted into fresh PWYE (OD 600 nm =0.1) and grown to mid-exponential phase before diluting into CCY (Stewart, G. S. A. B., Johnstone, K., Hagelberg, E. and Ellar, D. J. (1981), *Biochem. J.,* 198, 101–106). Cells were harvested at mid-exponential phase, early stationary phase, and stages I, II, III, IV-V and VI of sporulation, as determined by phase-contrast microscopy. *E. coli* JM1O1(pIP173 transformant) cells were grown in L Broth containing 100 micrograms/milliliter ampicillin at 37° C. overnight and then diluted into fresh L Broth. Cells were harvested at mid-exponential phase, early stationary phase and 4 hours after the onset of stationary phase. For both *israelensis* and *E. coli,* cells were harvested by centrifugation at the appropriate growth stage and RNA extracted using the glassbead (B. Braun Merlungen 0.1-0.11 mm diameter) breakage method. The extracted nucleic acids were hybridized to the 393 bp TaqI-BamHI probe shown in FIG. 5(*c*). The S1 resistant hybrids were denatured and analyzed using 4–6% acrylamide/8M urea gels. mRNA encoding the protein toxin gene was not detected in *israelensis* cells harvested at mid-exponential, early stationary, nor stage I of sporulation. However, gene specific RNA was detected in cells at stages II, III, IV, V and VI of sporulation. The S1 start point displays some heterogeneity, which could either be due to adjacent initiation sites being used in vivo, or due to an in vitro artifact generated during S1 nuclease digestion. Multiple initiation sites for both eucaryotic and procaryotic genes have been observed by others. The present results clearly indicate that the *israelensis* 27-kdal protein toxin gene is only transcribed during stages II-VI of sporulation, and that a unique start point is used. The amount of gene specific RNA appears to increase dramatically during stages I-II and then remain relatively constant at this level throughout sporulation. The probable start point, centered at nucleotide 238, used in *israelensis,* is shown in FIG. 4(*b*) (designated PBl). In addition, 3 other probes which span this 5′ region from different restriction sites have been used, and yield the same result.

For *E. coli,* using the 393 bp TaqI-BamHI probe, RNA was analyzed that had been extracted from cells harvested at the various stages of growth indicated. The one specific RNA is produced by cells during all three stages of growth, but as the cells enter stationary phase, the RNA appears to be less abundant or to undergo degradation, and the start points become less well defined. In contrast to the findings with var. *israelensis,* at least two start points appear to be used. The major transcriptional start point is the same as that used by var. *israelensis* (PBl), and the band of higher mobility represents complete protection of the 393 bp probe from S1 nuclease digestion. This latter species was investigated further using a 194 bp AhaII-AccI probe (FIG. 5(*c*) which extends 121 bp to the 5′ side of nucleotide 214 (FIG. 4(*b*)) (TaqI site). Using this probe, another start point (designated PECl) centered at nucleotide 104 (FIG. 4(*b*)) was found. In addition, some *E. coli*

RNA species gave complete protection of this probe, indicating that a start point to the 5′ side of nucleotide 92 (AhaII site) is also used. This species has not been investigated further. For both *israelensis* and *E. coli* a bandset of about 47 bp was observed using the 194 bp AhaII-AccI probe, consistent with the location of a start point at PBl.

Thus, S1 nuclease mapping has been used to locate the transcriptional start points for the 27-kdal protein toxin gene in *israelensis* and *E. coli.* For *israelensis,* the data indicates that transcription of the gene does not start until stage II of sporulation, and continues until the end of sporulation (stage VI). The same start point (PBl) is utilized from stage II until VI. The *israelensis* 27-kdal protein toxin gene thus differs from the var. *kurstaki* Pl delta-endotoxin, where 2 start points were found to be used differentially during stages II to VI of sporulation.

In *E. coli,* transcription of the *israelensis* protein toxin gene initiates from at least three different start points (PBl, PECl and an unidentified position). In addition, the *E. coli* transcripts are made during mid-exponential growth and then decrease during the stationary phase. This may be due to the deleterious effects of expression of the protein toxin gene, as the plasma membrane of *E. coli* contains at least one of the specific phospholipid targets of the protein toxin. The level of expression of the protein toxin gene in *E. coli* is low compared to that observed in *israelensis,* possibly for the reasons discussed above, but also due to the lack of substantial homology between the −10 and −35 regions corresponding to PBl and PECl and the consensus sequences for the −10 and −35 regions of promoters recognized by *E. coli* RNA polymerase containing sigma 70 as shown below.

| Holoenzyme/Promoter | Region −35 | Spacing | Region −10 |
|---|---|---|---|
| *E. coli:* | | | |
| E-sigma70 | TTGACA | 16–18 | TATAAT |
| var. *israelensis:* | | | |
| PB1 | GCATCT | 16 | TAGAAT |
| PEC1 | TTATTA | 16 | TCTTTT | corresponding −35 regions bear no resemblance to each other. For PECI, both the −10 and −35 regions have 3/6 bases in common with the corresponding consensus *E. coli* Sigma 70 sequences, assuming that for an *E. coli* promoter the optimal spacing between the −10 and −35 regions is 16-18 bp. There is a sequence between nucleotides 91–99 (FIG. 4(*b*) which shows reasonable homology (6/9 bp) with the −10 consensus sequence (CCCCATTTA) reported to be recognized by *E. coli* RNA polymerase containing Sigma 32. Comparison of the other −10 and −35 regions of PBl and PECI with the corresponding sequences for *E. coli* Sigma 32 RNA polymerase, however, has revealed little homology. However, a recent report in which the effect of promoter mutations on the expression of the tetA gene has been studied indicates that promoter-specific elements may, in some cases, be distributed along the DNA sequences over distances longer, but seldom less, than the 17±2 bp consensus distance.

When the nucleotide sequence for the −10 (TAGAAT) and −35 (GCATCT) regions of PBl is compared with the consensus sequences reported to be recognized by the different forms (modified by different Sigma factors) of *B. subtilis* RNA polymerase, particularly those known to be involved in the transcription of sporulation specific genes, no significant homologies are found. Interestingly, comparison of the −10 and −35 regions of PBl wth the corresponding sequences of the Btl promoter of the var. *kurstaki* delta-endotoxin gene shows that the regions share some homology (5/8 for the −10 region and 7/8 for the −35 region). This is of particular significance since transcription initiates from both PBl and Btl at stage II of sporulation in the respective strains of *B. thuringiensis.* There is in addition an extremely A+T rich box upstream of PBI, shown underlined in FIG. 4(*b*) which has also been found in var. *kurstaki* and in the *B. subtilis* spoVG promoter. For the spoVG promoter, deletion analysis has shown that this A+T rich region plays an important role in enhancing transcription.

Examination of the sequences at the 3′ end of the 27-kdal protein toxin structural gene has revealed the presence of an IR element (shown in FIG. 4(*b*)) which can potentially form a stem and loop structure in the transcript made from this region, with a predicted delta-G value of −26.0 kcal. This is similar in both the 3′ location and free energy to the retroregulator for the var. *kurstaki* delta-endotoxin gene. In addition, S1 mapping experiments indicate that although some protein toxin transcripts terminate at this potential stem and loop structure, a significant proportion extends beyond this sequence. Preliminary results suggest that the length of the 27-kdal protein toxin transcript varies with the stage of sporulation at which the mRNA is extracted. Different 3′ termini of the var. *kurstaki* delta-endotoxin gene transcript have been observed in cells harvested during mid and late sporulation.

The data obtained in the S1 mapping and Western blotting experiments indicates that the temporal control of expression of the *israelensis* gene is at the transcriptional, rather than the translational, level. Transcriptional initiation at PBl generates an mRNA with an unusually long 5′ untranslated sequence; several reports have shown that the accessibility of the initiation codon and, to a lesser extent, the ribosome binding site are important determinants of the level of expression of a gene. Analysis of the predicted secondary structure for the mRNA in the region between nucleotides 401-800 indicates that the Shine-Dalgarno sequence and initiation codon may be in exposed regions as shown later. It is conceivable that this plays a role in enhancing protein toxin gene expression.

Western blotting has also been used to analyze the timing of the synthesis of the 27-kdal protein toxin in var. *israelensis.* The data obtained in the S1 mapping and Western blotting experiments indicates that the control of expression of the *israelensis* toxin gene is at the transcriptional, rather than translational, level.

As described in FIG. 4(*a*), the segment of the *Bacillus thuringiensis* var. *israelensis* 27-kdal protein toxin gene or the genetic material of *E. coli* JM1O1 contained in pIP173 or pIP174, has (1) an expression mechanism, such as a translational start signal (296), e.g. ATGGAA, no more than approximately 95 nucleotides in front of a Bam HI restriction site (393), (2) a ribosome binding site (257), e.g. AAGGA, preceding the translational start signal by approximately 11 nucleotides, (3) a promoter region preceding the translational start signal by up to about 295 nucleotides; and (4) a structural DNA gene segment that is an Open Reading Frame (ORF) continuing from the start unbroken to about 90 nucleotides beyond a Hinc II restriction site (952) or to a stop codon (1045), e.g. TAA. One or more transcription starting sites in the promoter region can precede the ribosome binding site, a promoter region preceding the translational start signal (ATG) by up to about 295 nucleotides e.g. from about 220 to 226 and/or 240 to 246. For example, this DNA composition (sequence) is homologous to a DNA segment coding for a 27-kdal protein present in the crystal of *Bacillus thuringiensis* var. *israelensis* and is capable of expression in a microorganism (bacterial) host, such as *E. coli* or a *Bacillus* strain (for example, *B. megaterium* or *B. subtilis*, etc.) or the like.

The invention also includes an expression mechanism for expressing a structural DNA composition coding for an expressible protein in a microorganism host which comprises a DNA composition substantially sequence homologous to the DNA coding for an expression mechanism in the gene coding for a protein present in a crystal from *B. thuringiensis*.

This expression mechanism comprises a DNA composition having substantial sequence homology to a plasmid segment of *B. thuringiensis* having a molecular mass of about 295 bases, which corresponds to FIG. 3, sections C to A, FIG. 4(a), base pair numbers from about 0 to 295 or FIG. 4(b), base pair numbers from about 1 to 509.

The expression mechanism includes with reference to FIG. 4(a) (1) a translational start signal no more than about 95 nucleotides in front of a BamHI restriction site, (2) a ribosome binding site preceding the translational start signal by approximately 11 nucleotides, (3) a promoter region preceding the translational start signal by up to about 295 nucleotides, and one or more specific promoter sites preceding the ribosome binding site, such as one or more promoters at 220 to 226 or 240 to 246 nucleotides. As S1 mapping experiments have shown, there are also several promoters in the sequence 1 to 509 (FIG. 4b) that are utilized differentially in recombinants derived from different microorganisms harboring the protein toxin gene.

The invention also includes a vector comprising an ability to transform a transformable non-sporulating or spore-forming microorganism and an insert including a heterologous DNA composition (sequence) hybridizable with a gene segment for a 27-kdal protein present in the crystal of *Bacillus thuringiensis;* preferably, the DNA composition (sequence) is hybridizable with a gene, or segment thereof, coding for an expressible 27-kdal protein present in the crystal of *Bacillus thuringiensis* var. *israelensis* and is capable of transforming a bacterial host, such as *E. coli*, a *Bacillus* strain (such as *B. megaterium* or *B. subtilis*, etc.) or the like.

For example, this includes a plasmid having the capability of replication in a bacterial host species and containing expressible heterologous DNA coding for a 27-kdal protein toxin and including an expression mechanism for said heterologous DNA that is recognized by the host species system but does not exhibit substantial growth phase limitations in the bacterial host species. Such a plasmid is prepared by (1) isolating from a crystal protein-producing strain of *Bacillus thuringiensis* a first fragment of DNA comprising an expressible heterologous DNA composition having a nucleotide sequence coding for the protein, (2) providing one or more other DNA fragments which contribute(s) an expression mechanism for heterologous DNA in a selected bacterial host other than *B. thuringiensis*, the expression mechanism being recognized by said host without exhibiting substantial growth phase limitations, and (3) ligating said first DNA fragment and said other fragment(s) in the correct arrangement for expression of the heterologous protein-producing DNA coding in said host. For example, the DNA has substantial sequence homology to plasmid pIP173 or pIP174 or a segment thereof that codes for a 27-kdal protein toxin, such as the base sequence of FIG. 3, section A to B.

The present invention further includes: (1) An essentially pure recombinant circular plasmid having an insecticidal 27-kdal protein gene, or segment thereof, from *Bacillus thuringiensis* var. *israelensis* characterized by a molecular size of approximately 1045 bases or nucleotides and a restriction endonuclease cleavage map as shown in FIGS. 5(a), 8c or 8d, the gene being defined by the section C clockwise to B in FIG. 5(a); (2) an essentially linearized plasmid DNA composition having an insecticidal 27-kdal protein toxin coding gene, or segment thereof, coding for an expressible protein substantially homologous to a protein present in the crystal of *Bacillus thuringiensis* var. *israelensis*, said gene characterized by a molecular size of approximately 1045 bases or nucleotides and a restriction endonuclease cleavage map as shown in FIG. 3, sections from C to B; and (3) a plasmid DNA composition having an insecticidal protein structural DNA gene or segment thereof, from *Bacillus thuringiensis* characterized by a molecular size of approximately 750 bases or nucleotides and a restriction endonuclease cleavage map as shown in FIG. 3, section A to B in FIG. 4(a), base pair number from about 296 to 1045 or FIG. 4(b), base pair numbers from about 509 to 1258.

One embodiment of the invention comprises a method of synthesizing within a microorganism (e.g. bacterial) host and expressing a selected (mature) protein or polypeptide having insecticidal activity, which comprises culturing the (bacterial) host, the (bacterial) host being transformed with a cloning vehicle or vector comprising a plasmid or DNA composition (sequence) or segment thereof described herein in FIGS. 3 or 4(a) or 4(b).

Thus, a microorganism, such as a (bacterial) host, is transformed by introducing thereinto heterologous DNA composition coded in a plasmid or a DNA composition having the nucleotide base sequence described herein and capable of being both transcribed and expressed in said microorganism. Preferably, the bacterial host into which the (recombinant) plasmid or heterologous DNA composition (sequence) or segment thereof (or progeny of such a modified host) is introduced is *E. coli* or a *Bacillus* strain (such as *B. megaterium* or *B. subtilis*, etc.) or the like.

Application in Bacillus subtilis

Plasmids are constructed using conventional technology as follows.

(a) pHV33 is derived from pBR322 (*E. coli*) and pC194 (*Staphylococcus aureus*). The plasmid pC194 is able to replicate in *B. subtilis* (Horinouchi, S. and Weisblum, B. (1982) *J. Bact.*, 150, 812-825), and confers chloramphenicol resistance (FIG. 6a).

(b) CampUC is derived by ligating HindIII-cut pUC12 (Messing, J. (1983) *Methods Enzymol*, 101, 20-78) to the HindIII pC194 fragment of pHV33 (FIG. 6b).

(c) CamTaq 10 and CamTaq 11 each contain a 1.2 kb TaqI restriction fragment from pIP174 carrying the *B. thuringiensis* var. *israelensis* protein toxin gene (FIG. 6 and 7) which was inserted into the AccI site in pUC12.

A recombinant plasmid containing the TaqI fragment in the orientation shown in FIG. 6e was selected for further study. This recombinant plasmid was subsequently cut with HindIII, and ligated to the HindIII pC194 fragment of pHV33. The two forms of recombinant plasmid obtained from this ligation, named CamTaq 10 and CamTaq 11, have the pC194 fragment in opposite orientations (FIG. 6c and 6d). (See FIGS. 7 and 8 for more detail of CamTaq 10 and CamTaq 11 construction.) Other materials having substantially the same characteristics for cloning can be used.

Extraction of plasmid DNA from B. subtilis

An alkaline extraction procedure was used, based on the method of Birnboim H. C. and Doly, J. (1979) *J. Biol. Chem.*, 24, 3189-3195, with the following modifications:

(i) Selected clones were grown in 5 ml 2xTY media with 4 micrograms/milliliter chloramphenicol at 37° C., shaking at 250 RPM overnight (2xTY media is 10 g yeast extract, 10 g tryptone and 5 g sodium chloride per liter of water).

(ii) 1.5 ml of culture was harvested per tube.

(iii) After the first ethanol precipitation, the pellet was dissolved in 200 microliters TE (10 mM Tris [tris(-hydroxymethyl)methylamine buffer]-HCl pH 8.0, 0.1 mM ethylene diaminetetraacetic acid (EDTA) and 2 microliters ribonuclease RNAase (10 mg/ml) added. The tube was incubated at 37° C. for 15 min. The DNA was purified by phenol/chloroform: extraction and a second ethanol precipitation step. The pellet was dissolved in 20 to 40 microliters TE and stored at $-20°$ C.

Restriction enzyme digestion of plasmid DNA

This was carried out in the salt buffers described by Maniatis, T., Fritsch, E. F. and Sambrook, J. (1982) in "Molecular Cloning: A Laboratory Manual", Cold Spring Harbor Laboratory, New York, except that bovine serum albumin (BSA) was added to a final concentration of 100 micrograms/milliliter. Medium salt buffer was used for ClaI and HindIII digestions, high salt buffer for BamHI and double digestions using BamHI and ClaI. 1 microliter of restriction enzyme (New England Biolabs) was added to a 20 microliter DNA-buffer mixture, and this was incubated for 1-2 hr at 37° C. Samples were analyzed by agarose gel electrophoresis.

The plasmids were digested with BamHI, ClaI and a mixture of BamHI and ClaI. The digests were analyzed by 1% agarose gel electrophoresis (FIG. 9). The sizes of restriction fragments were determined from this gel, and are shown in the left margin of FIG. 9. The orientation of the pC194 HindIII fragment relative to the recombinant pUC12 plasmid was deduced for CamTaq 10 and Camtaq 11 (FIG. 6c and d).

Electrophoresis (a) Sodium dodecyl sulfate polyacrylamide gel electrophoresis (SDS-PAGE) was conducted as described by Laemmli, U. K. (1970) *Nature*, 227, 680-685, with an acrylamide: N,N'-methylenebisacrylamide ratio of 100:1. Samples were solubilized by incubation for 4 min at 100° C. in gel sample buffer (Laemmli, U. K. and Favre, M. (1973) *J. Mol. Biol.*, 80, 575-599). Samples were applied to a 13% gel run at 20 mA until the Bromophenyl blue dye front reached the separating gel, when the current was increased to 25 mA. The gel was stained overnight at room temperature with 0.1% (w/v) Coomassie Brilliant Blue R in 50% (v/v) methanol, 10% (v/v) acetic acid and destained with 10% (v/v) propan-2-ol, 10% (v/v) acetic acid.

(b) Silver staining of polyacrylamide gels was a modified form of the method described by Giulan, G. G., Moss, R. L. and Greaser, M. (1983), *Anal. Biochem.*, 129, 277-287. The gel was stained and destained as in (a). The proteins were cross-linked by soaking for 30 min in 10% (v/v) glutaraldehyde, washed 3 times in distilled water, and left in water overnight. The gel was soaked in ammoniacal silver nitrate for approximately 3 min, then rinsed 3 times in distilled water and developed for 1 to 2 min by the method of Giulan, G. G., Moss, R. L. and Greaser, M. (1983), *Anal. Biochem.*, 129, 277-287, except that a 40% (w/v) formaldehyde solution in 10% methanol was used.

(c) Agarose gel electrophoresis was conducted as described by Maniatis, T., Fritsch, E. F. and Sambrook, J. (1982) in "Molecular Cloning: A Laboratory Manual", Cold Spring Harbor Laboratory, New York, in Tris-borate buffer.

Protoplast transformation of B. subtilis

The method used was a modified form of that described by Chang, S. and Cohen, S. N. (1979), *Molec. gen. Genet.*, 168, 111-115. The strain to be transformed was grown in 5 ml Penassay Broth at 30° C., standing overnight. 1 ml of the culture was inoculated into 50 ml Penassay Broth and grown at 37° C., shaking at 250 RPM, to midlog phase ($OD_{600nm}=0.4$).

The cells were harvested by centrifugation and resuspended in 5 ml SMMP with lysozyme at a concentration of 2 mg/ml. SMMP is a mixture of equal volumes of double strength SMM with quadruple strength Penassay Broth in which SMM is a mixture of 0.5 molar sucrose, 0.02 molar maleic acid, 0.02 molar magnesium chloride hexahydrate (adjusted to pH 6.5 using sodium hydroxide) (Chang, S. and Cohen, S. N. (1979), *Molec. gen. Genet.*, 168, 111-115). The suspension was incubated at 37° C. with gentle shaking, and protoplasting checked by microscopic examination. When >90% of the cells had protoplasted (about 1 hr) they were pelleted in a Beckman J2 21 centrifuge, using a JA20 rotor, at 3000 RPM for 10 min, with slow braking to prevent disruption of the protoplasts. The protoplasts were washed in SMMP and pelleted a second time, then resuspended in 2.5–5 ml SMMP, depending on the concentration of protoplasts desired in the transformation step.

0.1 to 2 micrograms of DNA was dissolved in 50 microliters TE and 50 microliters SMM in a sterile 10 ml Oakridge tube, and 0.5 ml of protoplast suspension was added. 1.5 ml polyethylene glycol 6000 was added, and the suspension mixed gently for 2 min. 5 ml of SMMP was added to dilute the polyethylene glycol, and the protoplasts were recovered by centrifugation at 3000 RPM for 10 min. The pellet was resuspended in 1 ml SMMP and incubated for 1.5 hr at 30° C. with gentle shaking. 0.1 ml aliquots of this protoplast suspension were plated onto DM3 (regeneration) agar, and onto DM3 agar containing chloramphenicol at a concentration of 5 micrograms/milliliter or 10 micrograms/milliliter. Colonies were counted after incubation for 24 hours at 37° C. DM3 agar is a 1:1 mixture of the following quantities of solutions (sterilized separately): at 45° C. to 50° C.:

200 ml 4% agar,
500 ml 1 molar sodium succinate, pH 7.3, 100 ml 5% casamino acids,
50 ml 10% yeast extract,
25 ml 20% glucose,
100 ml mixture of 3.5% $K_2HPO_4$ and 1.5% $KH_2PO_4$,
20 ml of 1 molar $MgC_2$ ($6H_2O$),
5 ml of 2% bovine serum albumin; chloramphenicol was added to the media when selecting for chloramphenicol-resistant transformants at a concentration of 5–10 micrograms per milliliter (Chang, S. and Cohen, S. N. (1979), *Molec. gen. Genet.*, 168, 111–115).

Samples taken before and after treatment with lysozyme were plated out onto nutrient agar and DM3 agar, in order to determine the number of viable cells in the cultures. Colonies were counted after incubation at 37° C. for 24 hr.

Selected transformants were maintained as colonies on L. Broth agar plates containing 5 micrograms/milliliter chloramphenicol, and also stored at −80° C. in 15% glycerol in L broth.

Time course of sporulation

To obtain synchronous sporulation of cultures, the selected clone was grown in 5 ml 2xSG at 30° C. standing overnight. From this culture, 1 ml was inoculated into 10 ml 2xSG, and grown at 37° C., shaking at 250 RPM. At $OD_{600nm}=0.6$, the 10 ml culture was added to 90 ml 2xSG in a liter. 2xSG is, per liter of water:
16 g nutrient broth, and
2 g KCl (which media was autoclaved and to which 1 ml each of the following sterile solutions were added per 200 ml:
200 millimolar calcium nitrate ($4H_2O$),
10% (w/v) $MgSO_4$. ($7H_2O$),
200 millimolar iron chloride.($6H_2O$),
4 milligrams per milliliter tryptophan,
20% (w/v) glucose,
20 millimolar manganese chloride.($4H_2O$) (Leighton, T. J. and Doi, R. H. (1970), *J. Biol. Chem.*, 246, 3189–3195).

At the desired time points, the $OD_{600nm}$ was measured. 3 ml of culture was harvested and kept at −80° C. until processed for SDS-PAGE. A loopfull of culture was examined by phase-contrast microscopy, to determine the stage of sporulation of the culture. The same method was used for growth and analysis of the spoOJ transformant, although sporulation did not occur.

From the growth curve of *B. subtilis*, it can be deduced that there are about $6.6 \times 10^7$ colony-forming units (CFU)/ml of culture at $OD_{600nm}=0.4$. Treatment with lysozyme reduced the CFU/ml 100- to 200-fold to about $8 \times 10^5$ on DM3 medium, and the CFU/ml was considerably lower on nutrient agar since protoplasts do not regenerate well on this medium. Treatment with polyethylene glycol reduced the CFU/ml a further 500-fold to less than $2.5 \times 10^3$. The percentage of viable cells, after lysozyme and polyethylene glycol treatment, that were transformed to chloramphenicol resistance by uptake of plasmid DNA, varied between 0.5% and 8%, depending on:

(a) the concentration of plasmid DNA during polyethylene glycol treatment: an increase in DNA concentration from 50 ng/ml to 500 ng/ml doubled the percentage of transformants.

(b) the plasmid: pHV33 and CampUC gave 2- to 5-fold more transformants than CamTaq 10 or CamTaq 11.

(c) the amount of chloramphenicol in the DM3 plates: approximately twice as many transformants grew on plates containing 5 micrograms/milliliter as on plates containing 10 micrograms/milliliter chloramphenicol. Non-transformed *B. subtilis* did not grow at either chloramphenicol concentration.

50 to 4000 transformants were obtained per microgram of DNA. This is considerably lower than the transformation frequencies of up to $10^7$/microgram DNA reported by Chang, S. and Cohen, S. N. (1979), *Molec. gen. Genet.*, 168, 111–115, but they also reported a total viable cell count of $1.1 \times 10^8$ in each transformation mixture, whereas a viable cell count of $<4000$ was obtained in each transformation mixture described here. To increase the transformation frequency, modification of both lysozyme and polyethylene glycol treatment of the protoplasts would be required. Factors affecting transformation frequency are discussed by Chang, S. and Cohen, S. N. (1979), *Molec. gen. Genet.*, 168, 111–115, and by Klebe, R. J., Hariss, J. V., Sharp, Z. D. and Douglas, M. G. (1983), *Gene*, 25, 333–341.

On all DM3 plates, there was a background of very small colonies (diameter $<0.5$ mm). These often grew confluently, making them difficult to count, but there were usually more than $10^4$ per transformation mixture. However, these colonies did not grow when replicated onto L. Broth plates containing 5 micrograms/milliliter chloramphenicol.

Preparation of samples for SDS-PAGE

The frozen pellets from the time course were thawed out, and resuspended in TAS (20% (w/v) sucrose in 50 mM Tris-acetate pH 8.0) to a final volume of 200 microliters. Lysozyme was added to a final concentration of 0.25 mg/ml, and the cells held at 0° C. for 5 min. 100 microliters of TE was added, and after 5 min 200 microliters of 2% Triton was added. After 5 min, 10 mM $MgSO_4$ was added (final concentration) and DNAase at 10 micrograms/milliliter. After 10 min incubation at room temperature, 300 microliters of TAS was added. The suspension was sonicated for about 1 min with 0.5 inch sonic probe (Dawes Instruments, London) and examined by microscopy for complete lysis of cells. Cold trichloroacetic acid was added to give a final concentration of 12.5% (w/v), and the samples held at 0° C. for 30 min. The precipitate was collected by centrifugation for 15 min at 10,000 g, and resuspended in 100 to 400 microliters gel sample buffer by agitation in a sonic bath and vortexing. The volume of gel sample buffer added to each sample was directly proportional to the $OD_{600nm}$ of the culture at the time of sampling, 400 microliters being added to stationary phase samples. 50 microliters of each sample was used for SDS-PAGE.

Western blotting

Protein samples fractionated by SDS-PAGE were transferred electrophoretically to nitrocellulose paper by the method of Towbin, H., Staehelin, T. and Gordon, J. (1979), PNAS, 76, 4350–4354. The blot was soaked in 3% BSA in TBS (0.9% NaCl, 10 mM Tris-HCl solution, pH 7.4) at room temperature for 30 min, to block additional protein binding sites on the paper. The blot was then incubated with a 1:500 dilution of rabbit polyclonal antibodies to the purified 27-kdal protein toxin (previous literature values 26,000–28,00 DA) from *B. thuringiensis* var. *israelensis* (Ward, E. S., Ellar, D. J. and Todd, J. A. (1984), *FEBS Letters*, 175, 377–381) for 2 hr at room temperature, with gentle agitation. The blot was washed 5 times in TBS, then incubated for 1 hr with a 1:2000 dilution of horseradish peroxidase-conjugated goat IgG against rabbit IgG. 0.05% Non-Idet P40 was added to this incubation. The blot was washed 6 times with TBS containing 0.1% (w/v) Triton, and developed by the method of Hawkes, R., Niday, E. and Gordon, J. (1982), *Anal. Biochem.*, 119, 142-147. After 3 to 5 min of development, the blot was washed with distilled water, dried with filter paper and stored in the dark.

*Evidence that B. subtilis* transformants maintain the intact plasmid

Plasmid DNA was extracted from *B. subtilis* 168 and *B. subtilis* spoOJ clones transformed to chloramphenicol resistance. Horizontal agarose gel electrophoresis showed that all clones contained a plasmid that comigrated with the original plasmid (FIG. 10*a*). Restriction cenzyme digestions of plasmid preparations with HindIII (FIG. 10*a*) or BamHI and ClaI (FIG. 9 and 10*c*and *b*) produced fragments of the sizes expected from the restriction maps of the plasmids CamTaq 10 and CamTaq 11 (FIG. 6*c* and 6*d*).

The following clones were selected for growth and analysis:

(i) A *B. subtilis* 168 clone containing CamTaq 11, named CT 11-2, (ii) A *B. subtilis* 168 clone containing pHV33, (iii) A *B. subtilis* spoOJ clone containing CamTaq 10, named CT 10-19, and (iv) A *B. thuringiensis* var. *israelensis* clone.

Vegetative growth of *B. subtilis* strains ceased after 4-5 hr at 37° C., shaking at 250 RPM. This time is designated tO, and subsequent hourly intervals are designated $t_1$, $t_2$, $t_3$, etc. The *B., subtilis* 168 cells were in stage II of sporulation (Losick, R. and Youngman, P. (1984), in "Microbial Development" (R. Losick and L. Shapiro, eds.), Cold Spring Harbor Laboratory, New York) at about the third hour of sporulation (t3), as observed by phase contrast microscopy (with lysozyme added to the loopfull of cells). This coincided with a second increase in $OD_{600nm}$. The spoOJ strain did not sporulate, but the OD began to fall after $t_3$, as the cells lysed. Crystal inclusions were first observed in some CT 11-2 and CT 10-19 cells at $t_5$. *B. thuringiensis* var. *israelensis* grew faster than *B. subtilis* in 2×SG medium; and most cells contained fully-formed spores after 10 hr.

Samples of cells taken during growth and sporulation of *B. thuringiensis* var. *israelensis* were prepared for SDS-PAGE. The 27-kdal polypeptide was not detectable during vegetative growth, and was first detectable about one hour after onset of sporulation ($t_1$, ). It increased in amount during sporulation, as did the amount of the other crystal polypeptides. Samples taken during growth and sporulation of 168 CT 11-2 were also analyzed by SDS-PAGE. A 27-kdal polypeptide appeared during sporulation. Control samples from a *B. subtilis* clone transformed with pHV33 did not contain detectable amounts of a 27-kdal polypeptide. A Western blot of the protein samples from all three bacterial strains showed that a 27-kdal polypeptide antigenically related to the var. *israelensis* natural 26,000-28,000 protein toxin was expressed during sporulation of CT 11-2, but not during sporulation of the clone containing pHV33. At low protein loadings the 27-kdal polypeptide was first detectable in CT 11-2 2 to 3 hr after the end of exponential growth ($t_2$ to $t_3$); this is when the cells are in stage II of sporulation, as observed by phase contrast microscopy. However, at higher protein loadings the 27-kdal polypeptide was detectable in CT 11-2 approximately 2 hr earlier than this. The amount of this polypeptide in the cells clearly increases dramatically during sporulation, however.

Production of the 27-kdal polypeptide in non-sporing (spoOJ) mutant of *B. subtilis*

Protein samples extracted from the spoOJ transformant, CT 10-19, during growth on 2xSG were fractionated by SDS-PAGE. A 27-kdal polypeptide was first detectable by Coomassie staining 2 to 3 hr after the end of exponential growth, and accumulated over the next 14 hr. This polypeptide was shown to be antigenically related to the natural var. *israelensis* 26,000-28,000 protein toxin by Western blotting. At high protein loadings, it is clear that the 27-kdal cross-reacting polypeptide was being synthesized in the mid-exponential phase of growth in the organism albeit in small amounts. As growth of this non-sporing strain is prolonged to a point at which spores would normally form in the wild type organism, it is shown that a dramatic increase in the amount of the 27-kdal cross-reacting polypeptide occurs.

Purification of crystals from a *B. subtilis* transformant

A *B. subtilis* 168 cl-one, CT 11-2, containing the plasmid CamTaq 11 was grown in 5 ml PWYE medium (Peptone Water Yeast Extract) containing 4 micrograms/milliliter chloramphenicol at 37° C. standing overnight. From this culture, 0.5 ml was inoculated into 10 ml PWYE and incubated at 37° C., shaking at 250 RPM. At $OD_{600nm}$=0.6, 3 ml of the culture was inoculated into 200 ml CCY medium as described by Stewart, G. S. A. B., Johnstone, K., Hagelberg, E. and Ellar, D. J. (1981), *Biochem. J.*, 198, 101-106 (containing 4 micrograms/milliliter chloramphenicol). After 28 hr incubation at 37° C., shaking at 250 RPM, sporulation had been completed and about 80% of the cells had lysed. The spores, crystals and remaining cells were harvested by centrifugation. Most of the cells were at the bottom of the pellet, so only the top ⅔ of the pellet was resuspended in 0.1 M NaCl, 10 mM ethylenediaminetetracetic acid (EDTA), and washed three times. Spores and crystals were separated using differential ultracentrifugation through a discontinuous sucrose density gradient, consisting of 11 ml 67%, 16 ml 72% and 8 ml 79% (w/v) sucrose in 50 mM Tris-HCl pH 7.5. Centrifugation was carried out at 25,000 RPM for 16 hr at 4° C. The crystal band was removed and washed 3 times in 0.1 M NaCl, 10 mM EDTA. The final pellet was resuspended in 0.1 M NaCl, 10 mM EDTA and stored at −20° C. 50 microliters of the crystal suspension was equivalent to 100 ml of the original culture.

Crystals formed a major band at the interface of the 67% (w/v) and the 72% (w/v) sucrose, whereas the spores formed a discrete pellet at the bottom of the gradient. A small number of vegetative cells were seen in the crystal fraction by microscopy. Analysis of the crystal preparation by SDS-PAGE showed that the crystals consisted of one polypeptide of molecular weight 27-kdal (FIG. 11, lane 3).

50 microliters of the crystal preparation was solubilized in 50 mM $Na_2CO_3$ (pH 10.5). SDS-PAGE of this sample after alkali solubilization showed that the 27-kdal polypeptide from CT 11-2 crystals was degraded to a 24-kdal polypeptide (FIG. 11, lane 4). A 24-kdal polypeptide was not detectable by Coomassie blue staining after alkali solubilization of var. *israelensis* crystals (FIG. 11, lane 7; FIG. 12*a*, lane 7), but a band was visible after silver staining of the gel (FIG. 12*b*, lane 7). Proteolysis of the 27-kdal polypeptide to a 24-kdal polypeptide during alkali solubilization of var. *israelensis* crystals has been previously observed (Thomas, PhD Thesis, Cambridge, 1984). This has been attributed to endogenous proteases in the crystals. The 27-kdal polypeptide from var. *israelensis* was degraded more extensively to a 24-kdal polypeptide when var. *israelensis* crystals were alkali-solubilized in the presence of CT 11-2 vegetative cells (FIG. 12, lane 2). This indicates that the 27-kdal polypeptide in the CT 11-2 crystals was being degraded by *B. subtilis* proteases active in the crystal preparation during alkali solubilization. Some of the minor proteins detectable in the CT 11-2 crystal preparation on SDS-polyacrylamide gels (FIG. 11, lane 3; FIG. 12*b*, lane 1) may be adherent proteases arising from the culture fluid, and proteases may be released from the small number of CT 11-2 cells remaining in the CT 11-2 crystal preparation. The pellet from alkali solubilization of the CT 11-2 crystals did not contain any detectable protein (FIG. 11, lane 5). 50% to 80% of the 27-kdal polypeptide was alkali-solubilized from var. *israelensis* crystals (FIG. 12, lanes 6, 7 and 9).

Mosquito gut extract was prepared by sonicating 50 Aedes mosquito larvae for 1 min in 1 ml 50 mM $Na_2CO_3$.HCl (pH 10.5), using a sonic bath. The mixture was centrifuged at 10,000 g for 3 min; the supernatant was removed and stored at −20° C. in 100 microliter aliquots. 50 microliters of alkali-solubilized crystal was incubated with 5 microliters gut extract for 3 min at 37° C; then 50 microliters of SDS gel sample buffer was added immediately.

Treatment of solubilized CT 11-2 crystals and native var. *israelensis* crystals with mosquito gut extract for 3 min results in an identical pattern of polypeptide bands of molecular weight less than 28-kdal on SDS-polyacrylamide gels (FIG. 12, lanes 4 and 8).

S1 nuclease mapping of the transcriptional start points

The start points for transcription of the 27-kdal protein toxin gene were determined using high resolution S1 mapping. RNA was isolated from the cells at the growth stages. The 393 bp TaqI-BamHI probe described earlier for the *E. coli* clone was used for the hybridizations.

During mid-exponential growth, *B. subtilis* clones 168-11 and OJ-19 use the same point of transcriptional initiation, mapping to a position that is very close to the TaqI site at nucleotide 214 (FIG. 4(*b*)). Initiation in this region is heterogeneous.

As the two recombinants enter the third hour of stationary phase, however, several changes occur in the pattern of recognition of the start points. Firstly, in both 168-11 and OJ-19, initiation appears to occur at the start point PBl used by *B. thuringiensis* var. *israelensis,* albeit at a low level. In both 168-11 and OJ-19 a new start point appears to be used during the third hour of stationary phase centered at nucleotide 466 (PBS1). For OJ-19, the level of transcripts originating from PBS1 appears to show a further increase from the third to sixth hour of stationary phase and then remains relatively constant, and represents the major gene specific RNA for the following 11 hours. In contrast, the PBSI transcripts in 168-11 do not show this increase, and their level becomes undetectable at stages III-IV of sporulation. Concomitant with the decrease in the level of PBS1 transcripts, an increase in protein toxin transcription from other initiation points centered at nucleotide 390, (PBS2), and 238 (PB1), occurs. For 168-11, PBS2 and PB1 transcripts are the major gene specific RNA species during stages IV-VI of sporulation, whereas during the stationary phase of growth for OJ-19 these transcripts are only detectable at a low level.

When the *israelensis* 27-kdal protein toxin gene is cloned in a multicopy plasmid in two strains of *B. subtilis,* the toxin is expressed at a low level during vegetative growth in both strains. During stationary phase there is a marked increase in expression in both *B. subtilis* 168 and OJ. During sporulation of 168-11 and continued incubation of OJ-19, toxin synthesis is maintained at the high level and the protein is deposited as inclusions that are visible by phase contrast microscopy. Cells from stationary cultures of both these recombinants are toxic to *Aedes aegypti* larvae in vivo, and inclusions harvested from 168-11 are toxic to *Aedes albopictus* cells in vitro. Thus, following solubilization in alkaline buffer, the inclusions were assayed in vitro for toxicity against *Aedes albopictus* cells. After 20 hours, solubilized protein inclusions at a concentration of 0.5 microgram/milliliter had completely lysed $5\times10^4$ *Aedes albopictus* cells, with cytopathic effects which were indistinguishable from those caused by 2 micrograms/milliliter of alkali solubilized native *israelensis* crystals. In *in vivo* assays, purified toxin inclusions isolated from sporulated cultures of 168-11 caused death of third instar *Aedes aegypti* larvae, with an $LC_{50}$ of 125 ng/ml, whereas a lysate prepared from non-recombinant *B. subtilis* 168 cells had no detectable effect. Partially purified inclusions from OJ-19 showed similar potent larvicidal activity, but an $LC_{50}$ value was not obtained in this case. It is of significance that the 27-kdal protein toxin is able to produce phase-bright inclusions when it is produced in sufficient quantities. This has been observed for other cloned genes when they are expressed at high levels. Clearly, the simultaneous synthesis of the other polypeptides that occurs in the native *israelensis* crystal is not essential for formation of a protein inclusion body.

S1 nuclease mapping has been used to identify the transcriptional start points used by these two different recombinants Both 168-11 and OJ-19 utilize a very heterogeneous start point close to the TaqI site (at position 214) (FIG. 4(*b*)) during vegetative growth, and transcripts from this region are presumably responsible for the low level of protein toxin synthesis detected by Western blotting.

There is a transcriptional start site (PBl) used by *israelensis* 25 nucleotides downstream from the TaqI site, but in the constructs Camtaq 10 and 11 the −35 region is lacking from this promoter. Interestingly, *B. subtilis* 168 and OJ-87 appear to be able to utilize this start point as the cells enter stationary phase despite the apparent lack of some of the corresponding promoter sequences. A reason for the heterogeneity in initiation during vegetative growth may be that the appropriate transcription factors necessary to direct accurate initiation are not available. The possibility that the heterogeneous start point is due to readthrough transcription from fortuitously placed promoter sequences in the pC194 DNA is made unlikely by the fact that the pC194 orientation differs in Camtaq 10 and Camtaq 11.

The protein toxin gene is being expressed in a heterologous spore-forming organism (in 168-11) during vegetative growth, whereas in *israelensis* it is only expressed during sporulation. This is possibly due to the fact that the protein toxin gene is present in a multicopy plasmid in 168-11, and under these conditions trans-acting regulatory factors are titrated. This phenomenon has been observed for the cloned spoVG promoter. Alternatively, the lack of repression of the protein toxin gene in 168-11 may be due to the absence of suitable regulatory proteins in this recombinant, or sequences upstream of the TaqI site may be required for repression.

The data obtained from the S1mapping and Western blotting experiments, taken together, indicate that the appearance of transcripts originating from PBS1 and PBS2 coincides with a marked increase in protein toxin synthesis in 168-11 and OJ-19. This strongly suggests that it is the appearance of these transcripts after the onset of stationary phase, which results in the high level of protein toxin expression observed for these two recombinants. Clearly, transcriptional initiation at these points is temporally regulated, and two observations made during the S1 experiments are of particular interest.

Firstly, the OJ lesion, which prevents the first morphological manifestation of the sporulation process, does not appear to affect the temporally regulated transcription of the protein toxin gene from PBS1. The OJ lesion is the least pleiotropic stage 0 mutation, and an OJ lesion does not affect the transcription of genes that are affected by other stage 0 mutations. When the *israelensis* protein toxin gene is cloned in a *B. subtilis* 0A asporogenic strain using Camtaq 10, no increase in 27-kdal protein toxin expression is observed when the recombinant cells enter stationary phase.

Secondly, during the stationary phase of growth, 168-11 and OJ-19 use PBS1 and PBS2 differentially; 168-11 uses the start point at PBS1 transiently, and at a low level from stages I-III of sporulation, and PBS2 and PB1 transcripts become the major gene-specific mRNA during stages III-VI. In contrast, for OJ-19, PBS1 transcripts increase during the 3rd-4th hour of stationary phase, and are then maintained at a relatively high level for the following 14 hours. These observations are presumably due to differences in the availability and/or activity of certain regulatory proteins in *B. subtilis* 168 and OJ-87. The possibility that the orientation of the pC194 fragment in Camtaq 10 and 11 plays a role in affecting transcription from PBS1 and PBS2, although unlikely, cannot be excluded.

The −10 and −35 regions of PBS1 and PBS2 have been compared with the consensus sequences for the -10 and -35 regions of promoters recognized by *B. subtilis* RNA polymerase containing different sigma species as follows.

| Holoenzyme/ Promoter | Region −35 | Spacing | Region −10 |
|---|---|---|---|
| *B. subtilis:* | | | |
| Esigma[43] | TTGACA | 17–18 | TATAAT |
| Esigma[37] | AGG-TT | 13–16 | GG-ATTG-T |
| Esigma[32] | AAATC | 14, 15 | TA-TG-TT-TA |
| Esigma[29] | A-TT-AAAA | 14–17 | CATATT-T |
| Esigma[28] | CTAAA | 16 | CCGATAT |
| var. *israelensis:* | | | |
| PBS1 | GA<u>TT</u>AAT<u>AA</u> | 15 | CATAA<u>TTT</u> |
| PBS2 | ACATGCACC | 16 | A<u>ATATTAT</u> |

The −10 and −35 regions of PBS1 both have significant homologies (6/7 and 5/7 bases respectively) with the −10 and −35 consensus sequences for sigma[29] RNA polymerase, whereas for PBS2, only the -10 region (6/7 bases), but not the −35 region, has homology with the corresponding consensus sequences. Homologies between this -35 region and the consensus −35 regions corresponding to the different forms of *B. subtilis* RNA polymerase could not be found.

Since sigma[29] is only detectable in extracts of *B. subtilis* for a limited period during the stationaryphase of growth, this sigma factor could, in part, account for the temporal expression of the protein toxin from the PBS1 promoter. It is possible that sigma[29] cannot be detected in extracts of *B. subtilis* after stage III due to its compartmentalization into the forespore. This sequestration of sigma[29] from the mother cell could therefore account for the transient nature of transcriptional initiation from PBS1 in 168-11. Clearly, this compartmentalization cannot occur in OJ since stage 0 mutations prevent the formation of an asymmetric septum. In addition, the OJ lesion differs from the other stage 0 mutations in that it does not appear to affect the synthesis of sigma[29] The continued availability of sigma[29] in OJ cells could therefore account for the prolonged and high level of expression from PBS1 observed in OJ-19. In contrast, the expression of the protein toxin in 168-11 during stages III-VI of sporulation appears to be due to transcription f.rom PBS2 and PB1. It is conceivable that in OJ-19, continued utilization of PBS1 impairs transcriptional initiation at PBS2 and PB1. Alternatively, the availability of different regulatory factors in the two recombinants may be the major determinant of promoter recognition.

The ability of the *B. subtilis* recombinants 168-11 and OJ-19 to utilize multiple transcriptional initiation sites has been observed for several other *Bacillus* genes. For the wild type 168 strain particularly, the data herein suggests that this property contributes to the prolonged expression of the protein toxin gene throughout sporulation.

The invention also includes:

A transcription regulation sequence comprising a double stranded DNA segment selected from the group defined by base pair numbers of about 65 to 104, 90 to 104, 200 to 238, 224 to 238, 352 to 390, 376 to 390, 427 to 466 or 451 to 466 in FIG. 4(*b*) or the messenger RNA transcripts synthesized therefrom.

A promoter for gene expression comprising a double stranded DNA segment selected from the group defined by base pair numbers of about 65 to 75, 90 to 98, 200 to 210, 224 to 232, 352 to 362, 376 to 384, 427 to 437 or 451 to 459 in FIG. 4(*b*) or the messenger RNA transcripts synthesized therefrom.

Plasmids and DNA composition having the same or substantially equivalent nucleotide base sequences as described and claimed herein and clones as well as mutants and variants thereof or having taken up therein a foreign DNA composition or segment thereof at one of its restriction sites are prepared by conventional techniques and when having substantially the same biological properties to express 27-kdal protein toxin or smaller toxic segments thereof, including a segment of about 24- or 25-kdal, are included within the present invention. Proteins having the same or substantially equivalent amino acid sequences as described and claimed herein or toxic segments thereof and having substantially the same biological properties are included within the present invention.

The invention also includes a method for identifying a gene capable of expressing a 27-kdal protein toxin gene which comprises (1) hybridizing a probe consisting essentially of labeled DNA or RNA complementary to a DNA segment from a 750 base segment of DNA obtained from *Bacillus thuringiensis* var. *israelensis* shown in FIGS. 3 or 4(a) or (b), with a 27-kdal protein toxin gene source; (2) selecting exogenous DNA segments from said gene source that hybridize with said probe; (3) forming a recombinant DNA vector from said exogenous DNA segments and a vector; (4) transforming a host microorganism with said recombinant DNA vector; and (5) selecting transformed microorganisms that express a 27-kdal protein toxin.

Insecticidal activity

Although the immunoprecipitation of the in vitro synthesized cloned product showed clearly that a protein (polypeptide) antigenically related to the *israelensis* 26,000–28,000 Da natural delta-endotoxin was encoded by the 9.7 kb insert, additional experiments were needed to confirm that the polypeptide was biologically active. Lysates were therefore prepared from 1-liter cultures of clone colonies 173 and 174 and control *E. coli* JM101 colonies containing pUC12 lacking any *Bacillus thuringiensis* var. *israelensis* DNA insert and assayed for toxicity in vitro as described below.

Evidence that extracts of recombinant colonies 173 and 174 contained a biological activity essentially homologous to the 26,000 to 28,000 natural protein present in the crystal toxin from *B. thuringiensis* var. *israelensis* was obtained by assaying for insect toxicity in vivo using neonate *Aedes aegypti* larvae and in vitro using cultured cells of *Aedes albopictus*.

Extracts were prepared from 1-liter cultures of recombinant colonies 173 and 174 and control *E. coli* JM101 colonies containing pUC12 lacking any insert, and assayed for toxicity.

*In vitro toxicity assays* Recombinants were grown for 16 hr in L. Broth (Maniatis, T., Fritsch, E. F. and Sambrook, J. (1982) in "Molecular Cloning. A Laboratory Manual", Cold Spring Harbor Laboratory, N.Y.) containing 100 micrograms/ml$^{-1}$ ampicillin and harvested by centrifugation. Pellets from 1-liter cultures were resuspended in 12 ml 50 mM Na$_2$CO$_3$.HCl, pH 10.5, and disrupted by sonication. Five periods of 30 sec sonication with a 0.5 inch sonic probe (Dawe Instruments, London) operating at maximum intensity were sufficient to break more than 90% of the cells. The resulting lysate was incubated at 37° C. for 1 hr, and then saturated ammonium sulfate was added to a final concentration of 30%. The precipitate was pelleted by centrifugation and resuspended with 5 ml of 50 mM Na$_2$CO$_3$.HCl, pH 10.5 then 50–100 microliters of this suspension was added to a 4 cm Petri dish containing *Aedes albopictus* cells as previously described (De Barjac, H. (1978) C.R. Acad. Sci. Paris, ser. D 286, 797–800). Results were recorded using phase contrast microscopy and an Olympus OM2 camera attachment.

For *B. subtilis* clones, it was not possible to carry out a chemical determination of the protein content of the purified crystal preparation from CT 11-2, because only a small amount was prepared. Since an estimate of the protein content was necessary for comparison of the specific toxic activity of the cloned 27-kdal protein toxin with the native var. *israelensis* crystal protein toxin, protein concentrations were estimated by measuring the intensity of stained polypeptides after SDS-PAGE of known volumes of the two crystal preparations (FIG. 11).

*In vitro* toxicity assays showed 10 microliters of solubilized CT 11-2 crystal (about 0.7 microgram of 24-kdal polypeptide) to be consistently more toxic than 10 microliters of solubilized var. *israelensis* crystal (about 1.7 micrograms of 27-kdal polypeptide). After 20 hr, 5×10$^4$ *Aedes albopictus* cells had been fully lysed by about 0.5 microgram/milliliter of the CT 11-2 24-kdal polypeptide, whereas at least 2 micrograms/milliliter of the natural var. *israelensis* 27-kdal polypeptide was required to give the same effect.

The cells showed cytopathic effects typical of cells treated with the var. *israelensis* protein toxin, i.e. rapid rounding up followed sequentially by swelling, blebbing of membrane vesicles from the exterior of swollen cells, granulation of cell contents and finally cell lysis. Control cells exposed to 50 mM Na$_2$CO$_3$-HCl (pH 10.5) were unaffected after 20 hr.

The crystals from 50 microliters of *B. subtilis* crystal suspension were collected by centrifugation at 10,000 g for 5 min, and resuspended in 50 microliters 50 mM Na$_2$CO$_3$.HCl (pH 10.5). After incubation for 1 hr at 37° C., insoluble material was removed by centrifugation. A two-fold serial dilution of 10 microliters of supernatant was carried out in 50 mM Na$_2$CO$_3$.HCl pH 10.5, in a microtitre plate with 12 wells. 100 microliters of *Aedes albopictus* cells was added to each well. Cell density was determined using a haemocytometer counting chamber. 40 microliters of purified crystal from *B. thuringiensis* var. *israelensis* was solubilized and serially diluted in the same way. Control wells containing 100 microliters cells and 10 microliters 50 mM Na$_2$CO$_3$ were also set up. The pellet obtained from the alkali solubilization step was resuspended in phosphate-buffered saline (pH 7.0).

In vivo toxicity assays Recombinants were assayed for in vivo toxicity using a modification of the method of Tyrell, D. J., Davidson, L. I., Bulla, L. A., Jr. and Ramoska, W. A. (1979) *Appl. Environ. Microbiol.*, 38, 656-658). Recombinants were grown for 16 hr at 37° C. in L. Broth (Maniatis, T., Fritsch, E. F. and Sambrook, J. (1982) in "Molecular Cloning. A Laboratory Manual", Cold Spring Harbor Laboratory, New York) containing 100 microgram/ml$^{-1}$ ampicillin and harvested by centrifugation. Pellets from 100 ml culture were resuspended in 6 ml distilled water. 1.5 ml of this suspension was added to the cup containing 25 *A. aegypti* larvae. In vitro toxicity assays Protein extracted from recombinant colonies 173 and 174 caused cytolysis of *Aedes albopictus* cells, indistinguishable from that previously described for natural 26,000–28,000 delta-endotoxin (Thomas, W. E. and Ellar, D. J. (1983) *FEBS Lett.*, 154, 362–368). An amount of this protein extract equivalent to 6 ml of the original *E. coli* culture produced typical cytotoxicity (cell detachment, rounding, swelling and granulation) after 4 hr exposure to 5×10$^5$ Aedes cells, with complete lysis after 16 hr. By comparison with dose response curves for natural delta-endotoxin, this result indicates that the *E. coli* extract contains approximately 20 micrograms per milliliter of protein toxin. Aedes cells exposed to an equivalent protein extract from *E. coli* containing the vector PUC12 alone were unaffected even after prolonged exposure (24 hr).

The authenticity of the pIP173 and pIP174 encoded protein (polypeptides) was further confirmed by demonstrating that the toxicity of the recombinant colonies 173 or 174 lysates was neutralized either by polyclonal antibodies directed against the 26,000–28,000 Da native delta-endotoxin, or by preincubation of the lysates with sonicated preparations of those phospholipids previously shown to be the cell membrane receptors for authentic delta-endotoxin (Thomas, W. E. and Ellar, D. J. (1983) *FEBS Lett.*, 154, 362-368). As expected from the former result, addition of the delta-endotoxin-specific polyclonal antibodies to the 173 or 174 lysate precipitated a protein (27-kdal polypeptide) that was not detectable in control lysates.

Final confirmation of the biological authenticity of the cloned product was obtained from in vivo bioassays. 25 second instar *Aedes aegypti* larvae were killed in 4 hr when fed an amount of *E. coli* containing pIP173 or pIP174 equivalent to 25 ml of original culture. In control experiments larvae fed equivalent amounts of *E. coli* JM101 containing pUC12 with no insert were unaffected.

In vivo toxicity assays of *B. subtilis* clones were conducted in which 1.5 ml samples of bacterial cultures were taken during the time course, harvested, washed and resuspended in 0.1 M NaCl. This suspension was added to vials containing 10 to 15 *Aedes aegypti* larvae in 1.5 ml tap water.

At the end of sporulation, 1.5 ml of the 168 CT 11-2 and spoOJ CT 10-19 cultures were lethal to Aedes larvae, killing 95% of larvae within 3 hr. A similar result was obtained with the same volume of a sporulated culture of *B. thuringiensis* var. *israelensis*. The *B. subtilis* transformant containing pHV33 had no toxic effect on Aedes larvae at any stage during vegetative growth or sporulation. These results confirmed the authenticity of the 27-kdal polypeptide detected in CT 11-2 and CT 10-19 as the var. *israelensis* protein toxin (previous literature value 26,000-28,000).

Addition of a beta-galactosidase inducer, isopropyl-beta-D-thiogalacto-pyranoside (IPTG), to cultures of *E. coli* JM101 containing pIP173 or pIP174 did not result in an increase in toxin production measured in vitro. This suggests that expression of the delta-endotoxin gene in *E. coli* is under the control of *B. thuringiensis* promoter sequences rather than the vector beta-galactosidase promoter. In *B. thuringiensis* var. *israelensis* the purified 26,000-28,000 Da delta-endotoxin component of the crystalline inclusion represents approximately 15% of the total cell protein at the end of sporulation. As others (Schnepf, H. E. and Whiteley, H. R. (1981) *Proc. Natl. Acad. Sci. USA*, 78, 2893-2897; Held, G. A., Bulla, L. A., Jr., Ferrari, E., Hoch, J., Aronson, A. I. and Minnich, S. A (1982) *Proc. Natl. Acad. Sci. USA*, 79, 6065-6069; Klier, A., Fargett, F., Ribier, J. and Rapoport, G. (1982) *EMBO J.*, 1, 791-799) have observed for cloned lepidopteran-specific delta-endotoxin genes, the level of expression of the *israelensis* gene in *E. coli* is very low. This is not surprising in view of the lack of homology between *E. coli* consensus promoter sequences and promoters controlling *Bacillus* sporulation specific genes, exemplified here by the 27-kdal toxin gene (Losick, R. (1982) in: "The Molecular Biology of the Bacilli" (Dubnau, D. A. ed.), vol. 1, pp 179-201, Academic Press, New York; Wong, H. C., Schnepf, H. E. and Whiteley, H. R. (1983) *J. Biol. Chem.*, 258, 1960-1967).

The biologically active compounds of the invention (microorganisms and/or protein-containing products thereof) have been found to be toxic with respect to invertebrate pests, by which is meant insects of the class *Insecta*, especially of the order Diptera (especially larvae of mosquitoes and blackflies) and the like. Thus, the present invention also contemplates and includes: spores produced by microorganisms containing a DNA sequence described herein; an insecticidal composition comprising a microorganism; a lyophilizate; or other preservation form of a microorganism containing a plasmid or DNA composition sequence or segment thereof as disclosed above. For example, such a composition, upon dilution with water, or growth medium, produces a culture medium of the microorganism suitable for growth and protein expression. Also included in the invention is a protein of about 27,340 Da, that has been produced by a microorganism containing (coded in) such a plasmid or DNA sequence described herein and includes an insecticidal composition comprising a protein 27-kdal produced by a microorganism containing such a DNA composition (sequence), which protein is substantially homologous with a 26,000-28,000 Da protein present in the crystal from *Bacillus thuringiensis* var. *israelensis*.

Further, the invention includes a method of controlling insects at a locus comprising applying to the insects or to the locus an insecticidally effective amount of a microorganism or protein toxin of about 27,340 Daltons thereof produced by a microorganism containing such a plasmid or DNA composition sequence or segment thereof, including a method wherein the insects are in the larval stage.

For application, a compound of the invention ordinarily is applied most effectively by formulating it with a suitable, inert carrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting insect pests at a locus, which comprises applying to that locus a compound of the invention or an insecticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to by treated, or its storage, transport and/or handling. Any of the materials customarily employed in formulating pesticides—i.e., horticulturally acceptable adjuvants—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene;

petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lining sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25-75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, particularly for the protein, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is prent at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

DESCRIPTION OF THE PREFERRED EMBODIMENT

The gene encoding the 27-kdal protein toxin from *Bacillus thuringiensis* var. *israelensis* has been cloned into *Bacillus subtilis* on a multicopy plasmid. The plasmid is bifunctional, since it is able to replicate in *E. coli* and *B. subtilis*. The 27-kdal polypeptide has been shown to be selectively expressed during sporulation in *B. subtilis*, as it is in *B. thuringiensis* var. *israelensis*. This indicates that the 27-kdal protein toxin gene must be under similar regulatory control in both species. It has also been cloned into a mutant of *B. subtilis*, spoOJ, which does not exhibit any of the morphological characteristics of sporulation. When grown in identical conditions to a wild-type *B. subtilis* transformant (named CT 11-2), a spoOJ transformant (named CT 10-19) produces the 27-kdal polypeptide at the same time and in a similar quantity to the wild-type transformant. Crystal inclusions first appear in both transformant clones about five hours after the end of vegetative growth. Thus, crystal protein is formed free of spores in CT 10-19, and could be purified simply by centrifugation of the culture once most of the cells had lysed.

The 27-kdal protein toxin gene does not require the spoOJ gene product for its regulation and expression, since it is expressed normally in spoOJ mutants. The 27-kdal protein toxin is detectable in B. subtilis CT 11-2 transformants 1 hour after the end of vegetative growth, or 2 hours before prespores are beginning to form in the sPo+ strain (known as stags 1 of sporulation). In *B. subtilis* CT 10-19 transformants, synthesis of the 27-kdal protein toxin can be detected during vegetative (mid-exponential) growth.

In *B. subtilis*, protein toxin crystal inclusions form, which consist essentially solely of the 27-kdal polypeptide; whereas in *B. thuringiensis* var. *israelensis* the crystals also contain 5 other major polypeptides. Thus, it is probable that the 27-kdal polypeptide is able to self-assemble into a crystalline structure. When purified crystals from *B. subtilis* are solubilized in alkali (50 mM $Na_2CO_3$-HCl pH 10.5), the 27-kdal polypeptide is specifically degraded to a 24-kdal polypeptide. This is probably caused by *B. subtilis* proteases present in the crystal preparation, although it is possible that the 27-kdal polypeptide is autocatalytic. The 24-kdal polypeptide fragment has been shown to be more active in vitro than the solubilized 26,000-28,000 protein present in the crystals from *B. thuringiensis* var. *israelensis*. Thus, the complete 27-kdal polypeptide may not be necessary for toxic activity, and proteolytic cleavage may enhance its activity. The invention includes a protein of about 27-kdal or an insecticidally effective segment thereof, such as a 24- or 25-kdal segment or smaller insecticidally effective segment thereof, substantially free of other proteins, either as expressed by the microorganism or by subsequent recovery techniques. Thus, a protein of the invention is about 80%, 90% or 95% or higher purity in being free of other proteins.

The *E. coli* and *B. subtilis* cells as well as extracts isolated from the *E. coli* and *B. subtilis* recombinant clones were highly toxic to the larvae of *Aedes aegypti*. One preferred aspect of the present invention is the DNA composition (segment) of the 27-kdal toxin gene of *Bacillus thuringiensis* var. *israelensis* coding for an expressible protein toxin present in the crystal from *B. thuringiensis* var. *israelensis* and described above in accordance with FIGS. 3, 4(a) and 4(b) or having a nucleotide base sequence substantially as described above in accordance with FIGS. 4(a) or (b). This is incorporated into microorganisms (bacteria) by using known techniques of DNA transfer and/or sub-cloning to make vectors, or gene transfer vehicles, and clones having only the segment of the gene necessary to express a 27,340 Da protein toxin having an amino acid sequence substantially as described above in accordance with FIG. 4a and b, especially in crystalline form or an insecticidally effective segment thereof, such as a 24-kdal segment. Preferably, this protein toxin has mmunological cross-reactivity with antibodies for the natural 26,000-28,000 delta-endotoxin present in the crystal of *Bacillus thuringiensis* var. *israelensis* and is toxic to insects, including those of the order Diptera, especially larvae thereof. Thus, the microorganisms or protein-containing products thereof are useful as insecticides and especially as larvicides.

What is claimed is:

1. A recombinant plasmid capable of replication in a bacterial host species and containing an expressible heterologous DNA composition having a nucleotide base sequence coding for a 27kdal protein toxin or an insecticidally effective segment thereof and including an expression mechanism for said heterologous DNA which is recognized by the host species system but does not exhibit substantial growth phase limitations in the bacterial host species, the heterologous DNA composition having substantial sequence homology to the gene or gene segment coding for a protein present in a crystal of B. thuringiensis var. israelensis.

2. A plasmid according to claim 1 having a molecular mass of about 1045 bases in FIG. 4(a) or 1408 bases in FIG. 4(b) or the insecticidally effective 750 base structural DNA thereof.

3. A plasmid according to claim 3 including a heterologous DNA portion having substantial sequence homology to plasmid pIP173, pIP174, CamTaq 10 or CamTaq 11.

4. An essentially pure plasmid having a gene or segment thereof characterized by approximately 1045 bases in FIG. 4(a) or 1408 bases in FIG. 4(b) and a restriction endonuclease cleavage map as shown in FIG. 3, section C to B or a insecticidally segment thereof.

5. A plasmid according to claim 4 designated as sections A to B in FIG. 3 and variants thereof.

6. A DNA insecticidally composition comprising the 750 bases or segement thereof substantially as set forth in FIG. 3, section A to B, FIG. 4(a), base numbers 296 to 1045, or FIG. 4(b) base pair numbers 509-1258.

7. A DNA transfer vehicle comprising the nucleotide sequence according to claim 6.

8. A transcription regulation sequence comprising a double stranded DNA segment selected form the group defined by base pair numbers of about 65 to 104, 90 to 104, 200 to 238, 224 to 238, 352 to 390, 376 to 390, 427 to 466 or 451 to 466 in FIG. (b).

9. A promoter for gene expression comprising a double stranded DNA segment selected from the group defined by base pair numbers of about 65 to 75, 90 to 98, 200 to 210, 224 to 232, 352 to 362, 376 to 384, 427 to 437 or 451 to 459 in FIG. 4(b).

10. A microorganism transformed by a recombinant plasmid or a heterologous DNA composition thereof according to claim 1 and capable of being both transcribed and expressed in said microorganism.

11. A microorganism according to claim 10 which comprises a bacteria host into which a recombinant plasmid or heterologous DNA composition thereof according to claim 1 has been introduced.

12. A microorganism according to claim 10 which is *E. coli* or *B. subtilis*.

* * * * *

UNITED STATES PATENT AND TRADEMARK OFFICE
CERTIFICATE OF CORRECTION

PATENT NO. : 4,918,006

DATED : April 17, 1990

INVENTOR(S) : David J. Ellar and Elizabeth S. Ward

It is certified that error appears in the above-identified patent and that said Letters Patent is hereby corrected as shown below:

Column 34, line 19, change "of B. thuringiensis var. israelensis." to --of B. thuringiensis var. israelensis.--.

Column 34, line 24, change "according to Claim 3" to --according to Claim 2--.

Column 34, line 32, change "C to B or a insecticidally segment thereof." to --C to B or an insecticidally effective segment thereof.--.

Column 34, line 35, change "A DNA insecticidally composition comprising" to --An insecticidally effective DNA composition comprising--.

Column 34, line 36, change "segement" to --segment--.

Column 34, line 42, change "form" to --from--.

Column 34, line 45, change "FIG.(b)." to --FIG. 4(b).--.

Signed and Sealed this

Fifth Day of May, 1992

Attest:

DOUGLAS B. COMER

Attesting Officer

Acting Commissioner of Patents and Trademarks